US012624071B2

(12) United States Patent
Nguyen et al.

(10) Patent No.: US 12,624,071 B2
(45) Date of Patent: May 12, 2026

(54) BRIGHT AND STABLE RED FLUORESCENT PROTEIN

(71) Applicant: Triad National Security, LLC, Los Alamos, NM (US)

(72) Inventors: Hau Thi Bich Nguyen, Los Alamos, NM (US); Geoffrey S. Waldo, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 638 days.

(21) Appl. No.: 18/193,002

(22) Filed: Mar. 30, 2023

(65) Prior Publication Data

US 2024/0327474 A1      Oct. 3, 2024

(51) Int. Cl.
*C07K 14/435* (2006.01)
*C12N 15/10* (2006.01)

(52) U.S. Cl.
CPC .... *C07K 14/43595* (2013.01); *C12N 15/1058* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,271,241 B2 | 9/2007 | Waldo | |
| 2002/0107362 A1 | 8/2002 | Thastrup et al. | |
| 2002/0123113 A1 | 9/2002 | Tsien et al. | |
| 2002/0177189 A1 | 11/2002 | Bjorn et al. | |
| 2003/0013849 A1 | 1/2003 | Ward et al. | |
| 2015/0099271 A1* | 4/2015 | Waldo | G01N 33/542 435/23 |

FOREIGN PATENT DOCUMENTS

WO      WO 2013/176772 A1      11/2013

OTHER PUBLICATIONS

Csaba Kiss et al., "Directed evolution of an extremely stable fluorescent protein," Protein Engineering, Design & Selection, vol. 22, No. 5, pp. 313-323, (2009).
Hau B. Nguyen et al., "Split green fluorescent protein as a modular binding partner for protein crystallization," Acta Crystallographica Section D, Biological Crystallography, D69, 17 pages, (2013).
Nathan C. Shaner et al., "Improved monomeric red, orange and yellow fluorescent proteins derived from *Discosoma* sp. red fluorescent protein," Nature Biotechnology, vol. 22, No. 12, pp. 1567-1572, (Dec. 2004).

* cited by examiner

*Primary Examiner* — Suzanne M Noakes
*Assistant Examiner* — Jae W Lee
(74) *Attorney, Agent, or Firm* — Alston & Bird LLP

(57)      ABSTRACT

Improved Red Fluorescent Proteins (RFPs), nucleic acids encoding the improved RFPs, and methods of generating improved RFPs are described. The improved RFP can be used to form fusion molecule and can be used in applications for which fluorescent proteins are used.

8 Claims, 7 Drawing Sheets

Specification includes a Sequence Listing.

BRIGHT AND STABLE RED FLUORESCENT PROTEIN

ACKNOWLEDGMENT OF GOVERNMENT SUPPORT

This invention was made with government support under GM098177 awarded by the National Institutes of Health. The government has certain rights in the invention.

SEQUENCE LISTING

The Sequence Listing written in file S167675.000_SeqListing_ST26.xml is 22 kilobytes in size, was created Mar. 22, 2023, and is hereby incorporated by reference

BACKGROUND

Fluorescent proteins widely used as protein tagging agents. GFP-like proteins are an expanding family of homologous, 25-30 kDa polypeptides sharing a conserved 11 beta-strand "barrel" structure. The GFP-like protein family currently comprises well over 100 members, cloned from various Anthozoa and Hydrozoa species, and includes red, yellow and green fluorescent proteins and a variety of non-fluorescent chromoproteins. A wide variety of fluorescent protein labeling assays and kits are commercially available, encompassing a broad spectrum of spectral variants. While fluorescent proteins having various spectral and stabilities have been identified, there remained a need for fluorescent proteins with improved spectral properties or increased stability.

SUMMARY

Described are improved red fluorescent proteins (RFPs) and nucleic acids encoding the improved RFGs.

In some embodiments, an improved RFP comprises an amino acid sequence having at least 80%, at least 85%, at least 90%, or at least 95% identity to: (a) SEQ ID NO: 15, wherein amino acid at position 17 is tyrosine, amino acid at position 57 is serine, amino acid at position 98 is isoleucine, amino acid at position 100 is lysine, amino acid at position 131 is glycine, and amino acid at position 135 is isoleucine, amino acid at position 176 is tryptophan, and amino acid at position 203 is threonine; (b) SEQ ID NO: 17 wherein amino acid at position 17 is phenylalanine, amino acid at position 57 is serine, amino acid at position 98 is isoleucine, amino acid at position 100 is lysine, amino acid at position 131 is glycine, and amino acid at position 135 is isoleucine, amino acid at position 176 is tryptophan, and amino acid at position 203 is threonine; or (c) SEQ ID NO: 19, wherein amino acid at position 3 is asparagine, amino acid at position 25 is tyrosine, amino acid at position 36 is tyrosine, amino acid at position 45 is arginine, amino acid at position 83 is phenylalanine, amino acid at position 114 is histidine, amino acid at position 115 is asparagine, amino acid at position 139 is arginine, amino acid at position 174 is histidine, and amino acid is at position 176 is histidine, amino acid at position 180 is isoleucine, and amino acid at position 219 is alanine (FIG. 7).

In some embodiments, an improved RFP comprises an amino acid sequence having at least 80%, at least 85%, at least 90%, or at least 95% identity to: (a) SEQ ID NO: 15, wherein amino acid at position 17 is tyrosine, amino acid at position 57 is serine, amino acid at position 98 is isoleucine, amino acid at position 100 is lysine, amino acid at position 131 is glycine, and amino acid at position 135 is isoleucine, amino acid at position 176 is tryptophan, amino acid at position 203 is threonine, amino acid 36 is histidine, amino acid 92 is threonine, amino acid 125 is leucine, amino acid 147 is threonine, amino acid 162 is asparagine, and amino acid 196 is aspartate; (b) SEQ ID NO: 17 wherein amino acid at position 17 is phenylalanine, amino acid at position 57 is serine, amino acid at position 98 is isoleucine, amino acid at position 100 is lysine, amino acid at position 131 is glycine, and amino acid at position 135 is isoleucine, amino acid at position 176 is tryptophan, amino acid at position 203 is threonine, amino acid 36 is histidine, amino acid 92 is threonine, amino acid 125 is leucine, amino acid 147 is threonine, amino acid 162 is asparagine, and amino acid 196 is aspartate; or (c) SEQ ID NO: 19, wherein amino acid at position 3 is asparagine, amino acid at position 25 is tyrosine, amino acid at position 36 is tyrosine, amino acid at position 45 is arginine, amino acid at position 83 is phenylalanine, amino acid at position 114 is histidine, amino acid at position 115 is asparagine, amino acid at position 139 is arginine, amino acid at position 174 is histidine, and amino acid is at position 176 is histidine, amino acid at position 180 is isoleucine, amino acid at position 219 is alanine, amino acid 92 is threonine, amino acid 125 is leucine, amino acid 147 is threonine, amino acid 162 is asparagine, and amino acid 196 is aspartate.

In some embodiments, an improved RFP comprises the amino acid sequence of SEQ ID NO: 15 (iRFD1), SEQ ID NO: 17 (iRFD2), or SEQ ID NO: 19 (iRFD3). In some embodiments, an improved RFP consists of the amino acid sequence of SEQ ID NO: 15, SEQ ID NO: 17, or SEQ ID NO: 19.

Any of the described improved RFPs can be provided as a fusion molecule. In some embodiments, the fusion molecule comprises the amino acid sequence of SEQ ID NO: 15, SEQ ID NO: 17, or SEQ ID NO: 19. The improved RFPs can be conjugate to a molecule of interest via a chemical linkage, optionally via a linker, or the improved RFP can be a fusion protein with another polypeptide.

Any of the described improved RFPs or RFP fusion polypeptides can be encoded by a nucleic acid. In some embodiments, a nucleic acid sequence encoding an improved RFP or an RFP fusion polypeptide is operatively linked to a promoter sequence to facilitate expression of the RFP or the RFP fusion polypeptide. In some embodiments, a nucleic acid sequence encoding an improved RFP or an RFP fusion polypeptide is provided on a nucleic acid vector. The nucleic acid vector can be, but is not limited to, an expression vector or a CRISPR construct.

Any of the described improved RFPs, RFP fusion polypeptides, or nucleic acids encoding an RFPs or an RFP fusion polypeptide, can be provided in a host cell. A host cell comprising a nucleic acid encoding an improved RFP or an RFP fusion polypeptide can be grown under conditions sufficient to express the RFP or an RFP fusion polypeptide. The expressed RFP or an RFP fusion polypeptide can be purified from other components of the host cell.

Methods of generating an RFP having improved spectral or stability properties are described. In some embodiments, the methods comprise: (a) performing directed evolution on a nucleic acid encoding the amino acid sequence of any one of SEQ ID NOs: 6-14, 16, and 18 to generate a library of nucleic acids encoding mutated proteins; (b) expressing the mutated proteins; and (c) selecting the mutated proteins having high fluorescence and/or high stability. In some embodiments, the mutated proteins selected in step (c) are subjected to one or more additional rounds of directed evolution. Directed evolution includes, but is not limited to, DNA shuffling or saturation mutagenesis or one or more codons. Other mutagenesis procedures can also be utilized in the directed evolution procedure. In some embodiments, selecting mutated proteins having high fluorescence and/or high stability comprises selecting mutant proteins having enhanced folding activity, increased folding kinetics, increased thermostability, or increased resistance to chemical denaturation compared to a protein having the amino acid sequence of SEQ ID NO: 4. Proteins having the amino acid sequence of SEQ ID NO: 6-14, 16, or 18 contain one or more destabilizing loops. The destabilizing loops contain the amino acid sequence of SEQ ID NOs: 1, 2, or 3. Thus, in some embodiments, the methods further comprise removing the one or more destabilizing loops from the nucleic acid encoding the selected mutated protein of step (c).

In some embodiments, methods of generating an RFP having improved spectral or stability properties comprises: (a) inserting into a nucleic acid sequence encoding the polypeptide of SEQ ID NO: 4 or SEQ ID NO: 5 one or more of: (i) a nucleic acid sequence encoding the amino acid sequence of SEQ ID NO: 1 between codons coding for Gly52 and Pro53, (ii) a nucleic acid sequence encoding the amino acid sequence of SEQ ID NO: 2 between codons coding for Asp101 and Gly 102, and (iii) a nucleic acid sequence encoding the amino acid sequence of SEQ ID NO: 3 between codons coding for Asp169 and Gly 170, thereby generating a parent nucleic acid; (b) performing directed evolution on the parent nucleic acid to generate a library of nucleic acids encoding mutated proteins; (c) expressing the mutated proteins; and (d) selecting one or more mutated proteins having high fluorescence and/or high stability. Directed evolution includes, but is not limited to, DNA shuffling or saturation mutagenesis or one or more codons. Other mutagenesis procedures can also be utilized in the directed evolution procedure. In some embodiments, the nucleic acid sequence encoding the amino acid sequence of SEQ ID NO: 2 is inserted between the codons coding for Asp101 and Gly 102 is used. In some embodiments, the nucleic acid sequence encoding the amino acid sequence of SEQ ID NO: 1 is inserted between the codons coding for Gly52 and Pro53, and the nucleic acid sequence encoding the amino acid sequence of SEQ ID NO: 3 is inserted between the codons coding for Asp169 and Gly 170 is used. In some embodiments, the mutated proteins selected in step (d) are subjected to one or more additional rounds of directed evolution. In some embodiments, selecting one or more mutated proteins having high fluorescence and/or high stability comprises selecting one or more mutant proteins having enhanced folding activity, increased folding kinetics, increased thermostability, or increased resistance to chemical denaturation compared to a protein having the amino acid sequence of SEQ ID NO: 4. In some embodiments, the method further comprises removing the nucleotide sequence encoding the polypeptide of SEQ ID NO: 1, SEQ ID NO: 2, and/or SEQ ID NO: 3 from the nucleic acid encoding the selected mutated protein of step (d).

Also described are nucleic acids useful of identifying RFPs having improved spectral or stability properties. The nucleic acids useful of identifying RFPs having improved spectral or stability properties contain one or more destabilizing loops (see FIG. 6). The destabilizing loops comprise: (a) a nucleic acid sequence encoding the amino acid sequence of SEQ ID NO: 1 which is inserted between codons coding for Gly52 and Pro53; (b) a nucleic acid sequence encoding the amino acid sequence of SEQ ID NO:

2 which is inserted between codons coding for Asp101 and Gly 102; and/or (c) a nucleic acid sequence encoding the amino acid sequence of SEQ ID NO: 3 which is inserted between codons coding for Asp169 and Gly 170 wherein the amino acid correspond to the amino acid sequence of SEQ ID NO: 4. Mutagenesis of these nucleic acids and identifying one or more mutations that compensates for the destabilizing loops can result in an improved RFP. In some embodiments, the nucleic acids useful of identifying RFPs having improved spectral or stability properties encode a polypeptide having the amino acid sequence of any of SEQ ID NOs: 6-14, 16, and 18.

BRIEF DESCRIPTION OF THE DRAWINGS

Figure 7:
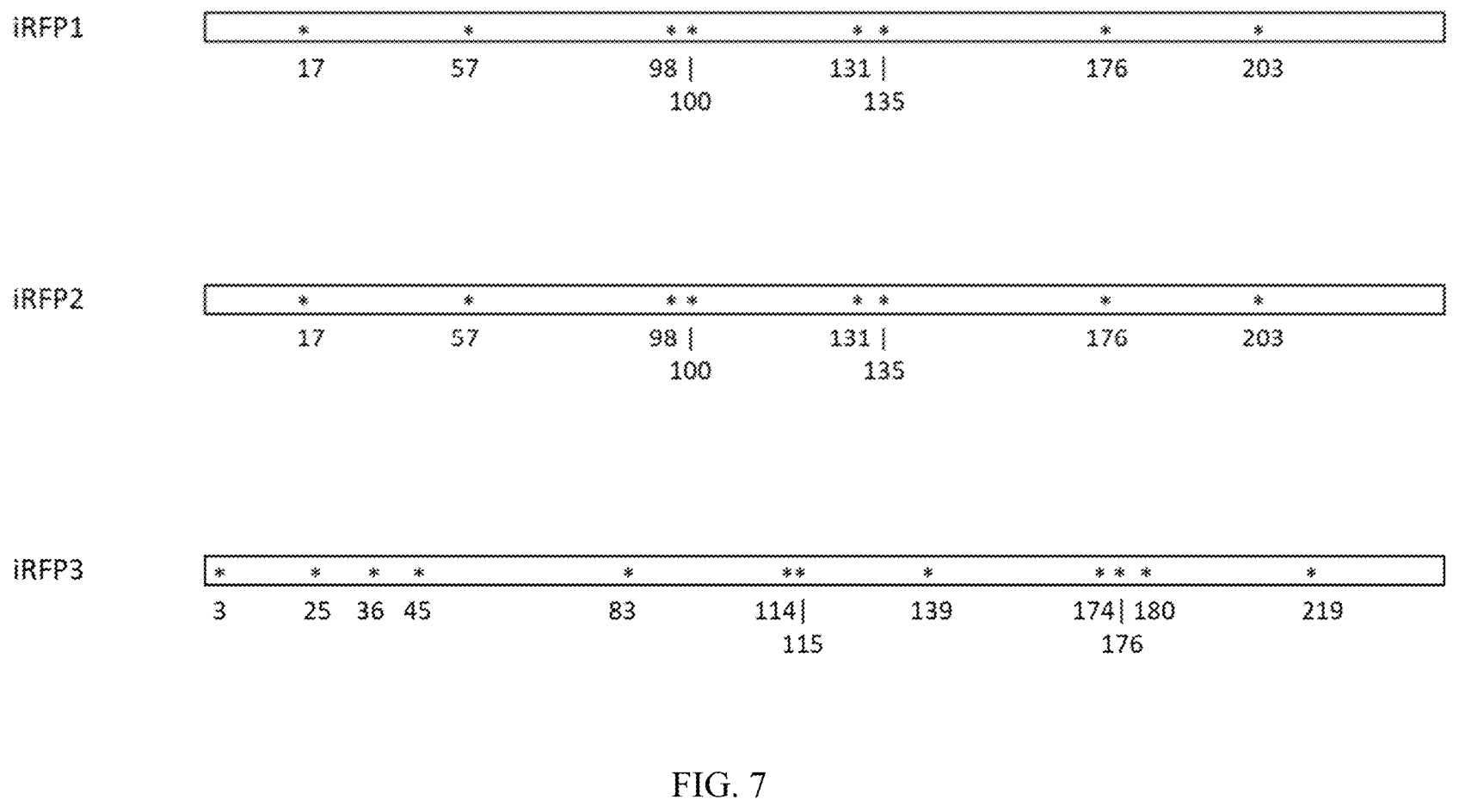

FIG. 7. Diagram illustrating amino acid positions where substitution resulted in improved red fluorescent proteins.

DETAILED DESCRIPTION

A. Definitions

Figure 1:
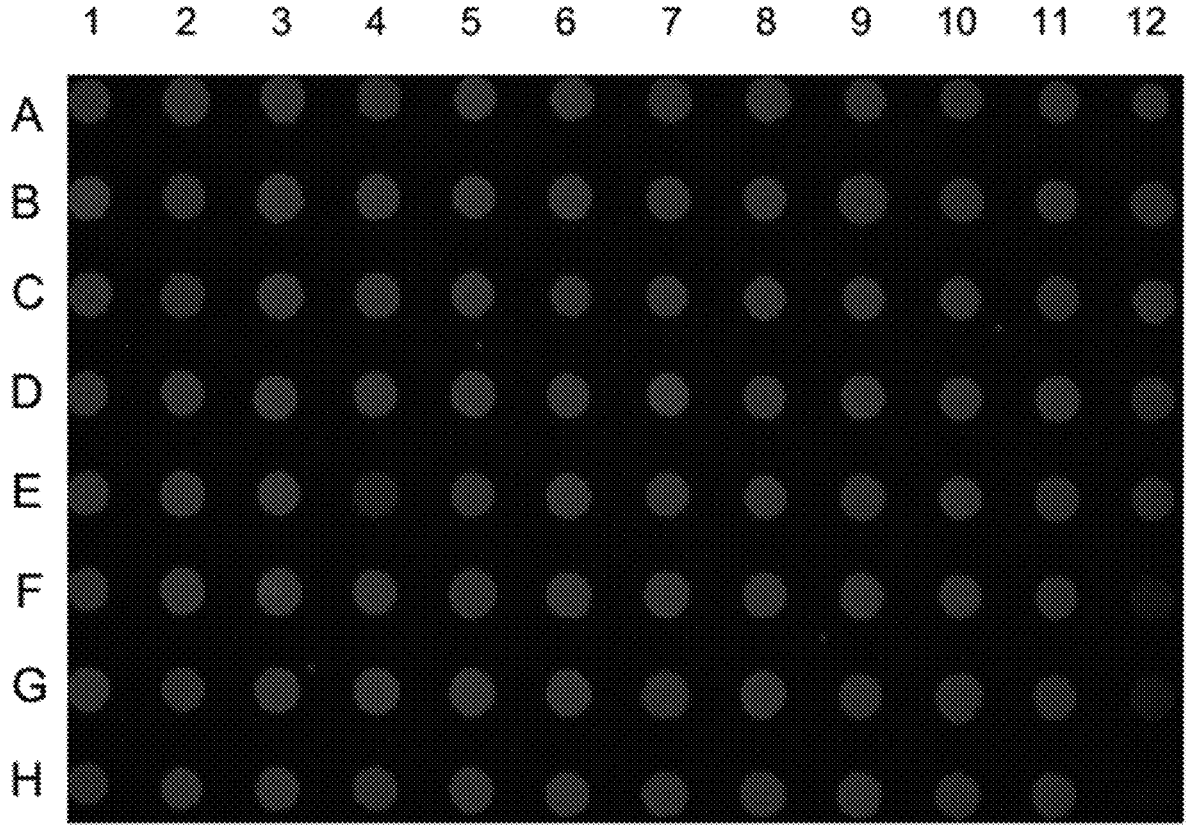
FIG. 1. Image illustrating directed evolution of sfCherry-loop2. Rows A to C: sfCherry-loop2 third round directed evolution. Rows D and E: sfCherry-loop2 best of second round directed evolution. Row F and G: sfCherry-loop2 best of first round directed evolution. Row H: sfCherry-loop2.

As used herein, the singular forms "a," "an," and "the" include plural referents unless the content clearly dictates otherwise. Thus, for example, reference to "a polypeptide" may include two or more such molecules, and the like.

As used herein, the terms "about" and "approximately," when used to modify an amount specified in a numeric value or range, indicates the numeric value as well as reasonable deviations from the value known to the skilled person in the art. In some embodiments, the term "about" means within the typical ranges of tolerances in the art. In some embodiments, the term "about" means within 1 or 2 standard deviations from the mean. In some embodiments, the term "about" means ±10%. In some embodiments, the term "about" means ±5%. When the term "about" is present before a series of numbers or a range, it is understood that "about" can modify each of the numbers in the series or range. The terms "polypeptide," "peptide" and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

The term "nucleic acid" refers to deoxyribonucleotides or ribonucleotides and polymers thereof ("polynucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19:5081; Ohtsuka et al., 1985 J. Biol. Chem. 260:2605-2608; and Cassol et al., 1992; Rossolini et al., 1994, Mol. Cell. Probes 8:91-98). The term nucleic acid is used interchangeably with gene, cDNA, and mRNA encoded by a gene.

"Operably linked" refers to the juxtaposition of two or more components (e.g., a promoter and another sequence element) such that both components function normally and allow the possibility that at least one of the components can mediate a function that is exerted upon at least one of the other components. For example, a promoter operably linked to a coding sequence will direct RNA polymerase mediated transcription of the coding sequence into RNA, including mRNA, which may then be spliced (if it contains introns) and, optionally, translated into a protein encoded by the coding sequence. A coding sequence can be "operably linked" to one or more transcriptional or translational control sequences. A terminator/polyA signal operably linked to a gene terminates transcription of the gene into RNA and directs addition of a polyA signal onto the RNA.

A "promoter" is a DNA regulatory region capable of binding an RNA polymerase in a cell (e.g., directly or through other promoter-bound proteins or substances) and initiating transcription of a coding sequence. A promoter may comprise one or more additional regions or elements that influence transcription initiation rate, including, but not limited to, enhancers. A promoter can be, but is not limited to, a constitutively active promoter, a conditional promoter, an inducible promoter, or a cell-type specific promoter. Examples of promoters can be found, for example, in WO 2013/176772.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine(S), Threonine (T); and 8) Cysteine (C), Methionine (M) (see, e.g., Creighton, Proteins (1984)). The term "vector" refers to a nucleic acid molecule capable of transporting another nucleic acid to which it has been linked. For example, one type of vector is a plasmid, a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into, the genome of a host cell upon introduction into the host cell, and thereby are replicated along with the host genome. Certain vectors are capable of directing the expression of genes to which they are operatively linked. Such vectors are referred to herein as "recombinant expression vectors" or "expression vectors".

The term "host cell" (or "recombinant host cell"), as used herein, refers to a cell that has been genetically altered, or is capable of being genetically altered by introduction of an exogenous polynucleotide, such as a recombinant plasmid or vector, and includes not only the particular subject cell but also the progeny thereof. Because certain modifications may occur in succeeding generations due to either mutation or environmental influences, such progeny may not, in fact, be identical to the parent cell, but are still included within the scope of the term "host cell" as used herein.

"Fused" refers to linkage by covalent bonding. As used herein, "linker" or "spacer" refers to a molecule or group of molecules that connects two molecules, such as VH and VL genes or polypeptides (i.e., in a scFv), and serves to place the two molecules in a preferred configuration.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "label" and "detectable label" refer to a detectable compound or composition which is conjugated directly or indirectly to the antibody so as to generate a "labeled" or "detectably labeled" antibody. The label may be detectable by itself (e.g. radioisotope labels or fluorescent labels) or, in the case of an enzymatic label, may catalyze chemical alteration of a substrate compound or composition which is detectable. A great number of such labels are known in the art, including without limitation protein tags, radioisotopes, metal chelators, enzymes, fluorescent compounds (dyes, proteins, chemicals), bioluminescent compounds, and chemiluminescent compounds.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a fluorescent protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acid or polypeptide sequences, refer to two or more sequences or subsequences that are the same or have a specified percentage of nucleic acid or amino acid residues (e.g., at least 60%, at least 65%, at least 70%), at least 75%, at least 80%>, at least 85%>, at least 90%, or at least 95% or greater) that are identical over a specified region when compared and aligned for maximum correspondence over a comparison window or designated region, as measured using a sequence comparison algorithm or by manual alignment and visual inspection. For sequence comparison, typically one sequence acts as a reference sequence to which a candidate sequence is compared. Alignment can be performed using various methods available to one of skill in the art, e.g., visual alignment or using publicly available software using known algorithms to achieve maximal alignment. Such programs include the BLAST programs, ALIGN, ALIGN-2 (Genentech, South San Francisco, Calif.) or Megalign (DNASTAR). The parameters employed for an alignment to achieve maximal alignment can be determined by one of skill in the art. For sequence comparison of polypeptide sequences for purposes of this application, the BLASTP algorithm standard protein BLAST for aligning two proteins sequence with the default parameters is used.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nuc. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

B. RFPs Having Improved Stability or Fluorescence

Described are improved red fluorescent proteins (RFPs) having high stability and fluorescence. Also described are constructs and methods for generating RFPs having high stability and fluorescence. The RFPs of the invention were derived from an artificial RFP known as sfCherry. Also provided a nucleic acids encoding the described RFPs and RFP constructs. The nucleic acids can be in a vector or host cell.

The described improved RFPs can have one or more of increase fluorescence, decreased background fluorescence, enhanced folding activity, increased folding kinetics, increased thermostability, or increased resistance to chemical denaturation compared to a protein having the amino acid sequence of SEQ ID NO: 4. In some embodiments, the described improved RFPs can have one or more of enhanced folding activity, increased folding kinetics, increased thermostability, or increased resistance to chemical denaturation compared to a protein having the amino acid sequence of SEQ ID NO: 5.

In some embodiments, an improved RFP comprises a protein having an amino acid sequence that is at least 80%, at least 85%, at least 90%, at least 95%, at least 96%, at least 97%, at least 98%, or at least 99% identical to the amino acid sequence of SEQ ID NO: 15, wherein amino acid 17 is tyrosine, amino acid 57 is serine, amino acid 98 is isoleucine, amino acid 100 is lysine, amino acid 131 is glycine, amino acid 135 is isoleucine, amino acid 176 is tryptophan, and amino acid 203 is threonine, wherein the indicated positions are in reference to SEQ ID NO: 15. In some embodiments, the improved RFP further comprises a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 15. In some embodiments, the improved RFP comprises the amino acid sequence of SEQ ID NO: 15. In some embodiments, the improved RFP consists of the amino acid sequence of SEQ ID NO: 15.

In some embodiments, an improved RFP comprises a protein having an amino acid sequence that is at least 80%, at least 85%, at least 90%, at least 95%, at least 96%, at least 97%, at least 98%, or at least 99% identical to the amino acid sequence of SEQ ID NO: 17, wherein amino acid 17 is phenylalanine, amino acid 57 is serine, amino acid 98 is isoleucine, amino acid 100 is lysine, amino acid 131 is glutamate, amino acid 135 is isoleucine; amino acid 176 is tryptophan, and amino acid 203 is asparagine, wherein the indicated positions are in reference to SEQ ID NO: 17. In some embodiments, the improved RFP further comprises a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 17. In some embodiments, the improved RFP comprises the amino acid sequence of SEQ ID NO: 17. In some embodiments, the improved RFP consists of the amino acid sequence of SEQ ID NO: 17.

In some embodiments, an improved RFP comprises a protein having an amino acid sequence that is at least 80%, at least 85%, at least 90%, at least 95%, at least 96%, at least 97%, at least 98%, or at least 99% identical to the amino acid sequence of SEQ ID NO: 19, wherein amino acid 3 is asparagine, amino acid 25 is tyrosine, amino acid 36 is tyrosine, amino acid 45 is arginine, amino acid 83 is phenylalanine, amino acid 114 is histidine, amino acid 115 is asparagine, amino acid 139 is arginine, amino acid 174 is histidine, amino acid is 176 is histidine, amino acid 180 is isoleucine, and amino acid 219 is alanine, wherein the indicated positions are in reference to SEQ ID NO: 19. In some embodiments, the improved RFP further comprises a threonine at amino acid 92, a leucine at amino acid 125, a threonine at amino acid 147, an asparagine at amino acid 162, and an aspartate at amino acid 196, wherein the indicated positions are in reference to SEQ ID NO: 19. In some embodiments, the improved RFP comprises the amino acid sequence of SEQ ID NO: 19. In some embodiments, the improved RFP consists of the amino acid sequence of SEQ ID NO: 19.

In some embodiments, any of the described improved RFPs can be provided as a fusion compound. The improved RFP can be fused to any molecule of interest. In some embodiments, the improved RFP is fused or linked to a protein or peptide. Linking the improved RFP to a protein or peptide can be done using any method available in the art for linking one protein or polypeptide to another. The fusion protein can also be made by creating an nucleic acid expression construct that expresses the fusion protein. Such fusion constructs can be made using methods available in the art for creating nucleic acid expression constructs expressing a fusion protein. In some embodiments, the RFP is fused to a protein of interest to facilitate imaging of the protein. In some embodiments, the RFP is fused to a tag sequence to facilitate purification of the RFP. Tag sequences include, but are not limited to, c-myc tag, HA-tag, polyhistidine (e.g., His6) tag, maltose binding protein, VSV-G tag, and anti-DYKDDDDK tag.

In some embodiments, an RFP fusion protein comprises a protein having an amino acid sequence that is at least 80%, at least 85%, at least 90%, at least 95%, at least 96%, at least 97%, at least 98%, or at least 99% identical to the amino acid sequence of SEQ ID NO: 15, wherein amino acid 17 is tyrosine, amino acid 57 is serine, amino acid 98 is isoleucine, amino acid 100 is lysine, amino acid 131 is glycine, amino acid 135 is isoleucine, amino acid 176 is tryptophan, and amino acid 203 is threonine, wherein the indicated positions are in reference to SEQ ID NO: 15. In some embodiments, the RFP fusion protein further comprises a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 15. In some embodiments, the RFP fusion protein comprises the amino acid sequence of SEQ ID NO: 15.

In some embodiments, an RFP fusion protein comprises a protein having an amino acid sequence that is at least 80%, at least 85%, at least 90%, at least 95%, at least 96%, at least 97%, at least 98%, or at least 99% identical to the amino acid sequence of SEQ ID NO: 17 wherein amino acid 17 is phenylalanine, amino acid 57 is serine, amino acid 98 is isoleucine, amino acid 100 is lysine, amino acid 131 is glutamate, amino acid 135 is isoleucine; amino acid 176 is tryptophan, and amino acid 203 is asparagine, wherein the indicated positions are in reference to SEQ ID NO: 17. In some embodiments, the RFP fusion protein further comprises a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 17. In some embodiments, the RFP fusion protein comprises the amino acid sequence of SEQ ID NO: 17.

In some embodiments, an RFP fusion protein comprises a protein having an amino acid sequence that is at least 80%, at least 85%, at least 90%, at least 95%, at least 96%, at least 97%, at least 98%, or at least 99% identical to the amino acid sequence of SEQ ID NO: 19, wherein amino acid 3 is asparagine, amino acid 25 is tyrosine, amino acid 36 is tyrosine, amino acid 45 is arginine, amino acid 83 is phenylalanine, amino acid 114 is histidine, amino acid 115 is asparagine, amino acid 139 is arginine, amino acid 174 is histidine, amino acid is 176 is histidine, amino acid 180 is isoleucine, and amino acid 219 is alanine, wherein the indicated positions are in reference to SEQ ID NO: 19. In some embodiments, the RFP fusion protein further comprises a threonine at amino acid 92, a leucine at amino acid 125, a threonine at amino acid 147, an asparagine at amino acid 162, and an aspartate at amino acid 196, wherein the indicated positions are in reference to SEQ ID NO: 19. In some embodiments, the RFP fusion protein comprises the amino acid sequence of SEQ ID NO: 19.

C. Nucleic Acids Encoding the Improved RFPs

Any of the improved RFPs can be encoded by a nucleic acid. Accordingly, also described are nucleic acid encoding any of the described improved RFPs.

In some embodiments, a nucleic acid encoding an improved RFP comprises a nucleic acid encoding a protein having an amino acid sequence that is at least 80%, at least 85%, at least 90%, at least 95%, at least 96%, at least 97%, at least 98%, or at least 99% identical to the amino acid sequence of SEQ ID NO: 15, wherein amino acid 17 is tyrosine, amino acid 57 is serine, amino acid 98 is isoleucine, amino acid 100 is lysine, amino acid 131 is glycine, amino acid 135 is isoleucine, amino acid 176 is tryptophan, and amino acid 203 is threonine, wherein the indicated positions are in reference to SEQ ID NO: 15. In some embodiments, the nucleic acid encoding the improved RFP further encodes a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 15. In some embodiments, the nucleic acid encoding the improved RFP comprises a nucleic acid sequence encoding the amino acid sequence of SEQ ID NO: 15. In some embodiments, the nucleic acid encoding the improved RFP encodes the amino acid sequence of SEQ ID NO: 15.

In some embodiments, a nucleic acid encoding an improved RFP comprises a nucleic acid encoding a protein having an amino acid sequence that is at least 80%, at least 85%, at least 90%, at least 95%, at least 96%, at least 97%, at least 98%, or at least 99% identical to the amino acid sequence of SEQ ID NO: 17, wherein amino acid 17 is phenylalanine, amino acid 57 is serine, amino acid 98 is isoleucine, amino acid 100 is lysine, amino acid 131 is glutamate, amino acid 135 is isoleucine; amino acid 176 is tryptophan, and amino acid 203 is asparagine, wherein the indicated positions are in reference to SEQ ID NO: 17. In some embodiments, the nucleic acid encoding the improved RFP further encodes a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 17. In some embodiments, the nucleic acid encoding the improved RFP comprises a nucleic acid sequence encoding the amino acid sequence of SEQ ID NO: 17. In some embodiments, the nucleic acid encoding the improved RFP encodes the amino acid sequence of SEQ ID NO: 17.

In some embodiments, a nucleic acid encoding an improved RFP comprises a nucleic acid encoding a protein having an amino acid sequence that is at least 80%, at least 85%, at least 90%, at least 95%, at least 96%, at least 97%, at least 98%, or at least 99% identical to the amino acid sequence of SEQ ID NO: 19, wherein amino acid 3 is asparagine, amino acid 25 is tyrosine, amino acid 36 is tyrosine, amino acid 45 is arginine, amino acid 83 is phenylalanine, amino acid 114 is histidine, amino acid 115 is asparagine, amino acid 139 is arginine, amino acid 174 is histidine, amino acid is 176 is histidine, amino acid 180 is isoleucine, and amino acid 219 is alanine, wherein the indicated positions are in reference to SEQ ID NO: 19. In some embodiments, the nucleic acid encoding the improved RFP comprises a nucleic acid sequence encoding the amino acid sequence of SEQ ID NO: 19. In some embodiments, the nucleic acid encoding the improved RFP encodes the amino acid sequence of SEQ ID NO: 19.

Any of the described improved RFPs can be provided on nucleic acid encoding a fusion protein, wherein the nucleic acid encodes a polypeptide-RFP fusion protein.

In some embodiments, a nucleic acid encoding an RFP fusion protein comprises a nucleic acid encoding a protein having an amino acid sequence that is at least 80%, at least 85%, at least 90%, at least 95%, at least 96%, at least 97%, at least 98%, or at least 99% identical to the amino acid sequence of SEQ ID NO: 15, wherein amino acid 17 is tyrosine, amino acid 57 is serine, amino acid 98 is isoleucine, amino acid 100 is lysine, amino acid 131 is glycine, amino acid 135 is isoleucine, amino acid 176 is tryptophan, and amino acid 203 is threonine, wherein the indicated positions are in reference to SEQ ID NO: 15. In some embodiments, the nucleic acid encoding the RFP fusion protein further encodes a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 15. In some embodiments, the nucleic acid encoding the RFP fusion protein comprises a nucleic acid sequence encoding the amino acid sequence of SEQ ID NO: 15.

In some embodiments, a nucleic acid encoding an RFP fusion protein comprises a nucleic acid encoding a protein having an amino acid sequence that is at least 80%, at least 85%, at least 90%, at least 95%, at least 96%, at least 97%, at least 98%, or at least 99% identical to the amino acid sequence of SEQ ID NO: 17, wherein amino acid 17 is phenylalanine, amino acid 57 is serine, amino acid 98 is isoleucine, amino acid 100 is lysine, amino acid 131 is glutamate, amino acid 135 is isoleucine; amino acid 176 is tryptophan, and amino acid 203 is asparagine, wherein the indicated positions are in reference to SEQ ID NO: 17. In some embodiments, the nucleic acid encoding the RFP fusion protein further encodes a histidine at amino acid 36, a threonine at amino acid 92, a leucine at amino acid 125, a threonine at amino acid 147, an asparagine at amino acid 162, and an aspartate at amino acid 196, wherein the indicated positions are in reference to SEQ ID NO: 17. In some embodiments, the nucleic acid encoding the RFP fusion protein comprises a nucleic acid sequence encoding the amino acid sequence of SEQ ID NO: 17.

In some embodiments, a nucleic acid encoding an RFP fusion protein comprises a nucleic acid encoding a protein having an amino acid sequence that is at least 80%, at least 85%, at least 90%, at least 95%, at least 96%, at least 97%, at least 98%, or at least 99% identical to the amino acid sequence of SEQ ID NO: 19, wherein amino acid 3 is asparagine, amino acid 25 is tyrosine, amino acid 36 is tyrosine, amino acid 45 is arginine, amino acid 83 is phenylalanine, amino acid 114 is histidine, amino acid 115 is asparagine, amino acid 139 is arginine, amino acid 174 is histidine, amino acid is 176 is histidine, amino acid 180 is isoleucine, and amino acid 219 is alanine, wherein the indicated positions are in reference to SEQ ID NO: 19. In some embodiments, the nucleic acid encoding the RFP fusion protein further encodes a threonine at amino acid 92, a leucine at amino acid 125, a threonine at amino acid 147, an asparagine at amino acid 162, and an aspartate at amino acid 196, wherein the indicated positions are in reference to SEQ ID NO: 19. In some embodiments, the nucleic acid encoding the RFP fusion protein comprises a nucleic acid sequence encoding the amino acid sequence of SEQ ID NO: 19.

Also described are nucleic acids encoding RFPs having one or more destabilizing loops. The nucleic acids encoding RFPs having one or more destabilizing loops are useful in directed evolutions procedures for generating improved RFP having increased stability and/or spectral properties (increased fluorescence of decreased background fluorescence) .

In some embodiments, the nucleic acid encodes an RFP having a destabilizing loop inserted between codons coding for Gly52 and Pro53 of SEQ ID NO: 4 or 5. In some embodiments, the destabilizing loop comprises of consists of the amino acid sequence of SEQ ID NO: 1. In some embodiments, the nucleic acid encoding an RFP having a destabilizing loop inserted between codons coding for Gly52 and Pro53 comprises a nucleic acid encoding a protein having an amino acid sequence that is at least 80%, at least 85%, at least 90%, at least 95%, at least 96%, at least 97%, at least 98%, at least 99%, or 100% identical to the amino acid sequence of SEQ ID NO: 6 or SEQ ID NO: 7.

In some embodiments, the nucleic acid encodes an RFP having a destabilizing loop inserted between codons coding for Asp101 and Gly 102 of SEQ ID NO: 4 or 5. In some embodiments, the destabilizing loop comprises or consists of the amino acid sequence of SEQ ID NO: 2. In some embodiments, the nucleic acid encoding an RFP having a destabilizing loop inserted between codons coding for Asp101 and Gly 102 comprises a nucleic acid encoding a protein having an amino acid sequence that is at least 80%, at least 85%, at least 90%, at least 95%, at least 96%, at least 97%, at least 98%, at least 99%, or 100% identical to the amino acid sequence of SEQ ID NO: 8, SEQ ID NO: 9, SEQ ID NO: 14, or SEQ ID NO: 16.

In some embodiments, the nucleic acid encodes an RFP having a destabilizing loop inserted between codons coding for Asp169 and Gly 170 of SEQ ID NO: 4 or 5. In some embodiments, the destabilizing loop comprises or consists of the amino acid sequence of SEQ ID NO: 3. In some embodiments, the nucleic acid encoding an RFP having a destabilizing loop inserted between codons coding for Asp169 and Gly 170 comprises a nucleic acid encoding a protein having an amino acid sequence that is at least 80%, at least 85%, at least 90%, at least 95%, at least 96%, at least 97%, at least 98%, at least 99%, or 100% identical to the amino acid sequence of SEQ ID NO: 10 or SEQ ID NO: 11.

In some embodiments, the nucleic acid encodes an RFP having a first destabilizing loop inserted between codons coding for Gly52 and Pro53 and a second destabilizing loop inserted between codons coding for Asp169 and Gly 170 of SEQ ID NO: 4 or 5. In some embodiments, the first destabilizing loop comprises or consists of the amino acid sequence of SEQ ID NO: 1 and the second destabilizing loop comprises or consists of the amino acid sequence of SEQ ID NO: 3. In some embodiments, the nucleic acid encoding an RFP having the first destabilizing loop inserted between codons coding for Gly52 and Pro53 and the second destabilizing loop inserted between codons coding for Asp169 and Gly 170 comprises a nucleic acid encoding a protein having an amino acid sequence that is at least 80%, at least 85%, at least 90%, at least 95%, at least 96%, at least 97%, at least 98%, at least 99%, or 100% identical to the amino acid sequence of SEQ ID NO: 12, SEQ ID NO: 13, or SEQ ID NO: 18.

In some embodiments, the nucleic acid encodes an RFP having a first destabilizing loop inserted between codons coding for Gly52 and Pro53, a second destabilizing loop inserted between codons coding for Asp101 and Gly 102, and a third destabilizing loop inserted between codons coding for Asp169 and Gly 170 of SEQ ID NO: 4 or 5. In some embodiments, the first destabilizing loop comprises or consists of the amino acid sequence of SEQ ID NO: 1 and the second destabilizing loop comprises or consists of the amino acid sequence of SEQ ID NO: 2, and the third destabilizing loop comprises or consists of the amino acid sequence of SEQ ID NO: 3.

In some embodiments, a nucleic acid sequence encoding an improved RFP, an RFP fusion protein, or an RFP having one or more destabilizing loops is operatively linked to a promoter. The promoter drives expression of the RFP in a cell. The promoter can be a promoter that is active in a prokaryotic cell (prokaryotic promoter) or a eukaryotic cell (eukaryotic promoter). A prokaryotic promoter can be, but is not limited to, β-lactamase promoter, a lactose promoter systems, a tryptophan promoter, a tac promoter or a λ promoter. The eukaryotic promoter can be a promoter that is active in yeast cells, insect cells, or mammalian cells. A eukaryotic promoter can be, but is not limited to, a GAL promoter, an AOX 1 promoter, a β-actin promoter, metal-lothionein promoter, and viral promoters (e.g., CMV promoter, SV40 promoter, murine mammary tumor virus promoter, Rous sarcoma virus promoter).

In some embodiments, a nucleic acid sequence encoding an improved RFP, an RFP fusion protein, or an RFP having one or more destabilizing loops is provided in a vector. The vector can be, but is not limited to, a plasmid, an expression vector, a prokaryotic plasmid or expression vector, a eukaryotic plasmid or expression vector, or a viral vector, or a CRISPR construct. A prokaryotic plasmid or expression vector includes, but is not limited to, pET, pTET, pBR322-based plasmids (e.g., pBLUESCRIPT™, pSKF, pET23D), A-phage derived vectors, p15A-based vectors and fusion expression systems such as GST.

D. Methods of Manufacture

The disclosed improved RFPs, RFP fusion proteins, and RFP having one or more destabilizing loops may be expressed in a host cell suitable for expression of a heterologous protein. Such cells include, but are not limited to bacteria cells, eukaryotic cells, mammalian cells, insect cells, and yeast cells. Bacterial cells include, but are not limited to E. coli cells. In some embodiments, a nucleic acid encoding the improved RFP is introduced into the host cell. A nucleic acid encoding an improved RFP can be introduced into a host cell using any method available in the art for introducing a nucleic acid encoding an expressible polypeptide into a cell.

The disclosed improved RFPs, RFP fusion proteins, and RFP having one or more destabilizing loops can be expressed intracellularly or they can be secreted from the cell. In some embodiments, the amount of soluble, active polypeptide may be increased by performing refolding a procedures (see, e.g., Sambrook et al.; Marston at al., Bio/Technology (1984) 2:800; Schoner at al., Bio/Technology (1985) 3:151).

Once expressed, improved RFPs, RFP fusion proteins, and RFP having one or more destabilizing loops can be purified using any method available in the art for purification of proteins expressed in a host cell. Such methods include, but are not limited to, ammonium sulfate precipitation, affinity columns, column chromatography, and gel electrophoresis.

In some embodiments, an improved RFP is fused to an epitope or tag that facilitates purification. Epitopes and tags include, but are not limited to, HA tag, myc tag, and polyhistidine tag.

In some embodiments, methods of generating the improved RFPs, RFP fusion proteins, and RFP having one or more destabilizing loops comprise introducing a expression vector encoding the improved RFP, RFP fusion protein, or RFP having one or more destabilizing loops into a host cell, incubating the host under conditions suitable for expression of the improved RFP, RFP fusion protein, or RFP having one or more destabilizing loops, and purifying the expressed improved RFP, RFP fusion protein, or RFP having one or more destabilizing loops from one or more components of the host cell.

E. Methods of Generating RFP Having Improved Stability or Fluorescence

Described are methods for generating stability-enhanced RFPs. In some embodiments, the methods comprise inserting one or more destabilizing loops into an RFP (e.g., SEQ ID NO: 4 or SEQ ID NO: 5), performing directed evolution to form mutant RFPs, expressing the mutant RFPs, and screening the expressed mutant RFPs for increased stability and/or fluorescence. In some embodiments, the methods further comprise removing the destabilizing loops from the mutant RFPs. In some embodiments, two or more rounds performing directed evolution, expressing the mutation RFP proteins, and screening the expressed mutant RFPs for increased stability and/or fluorescence are used. Performing directed evolution comprises introducing one or more mutations into the nucleic acid sequence encoding the protein. Performing directed evolution includes, but is not limited to, DNA shuffling or saturation mutagenesis or one or more codons. Screening the expressed mutant RFPs for increased stability and/or fluorescence can include, but is not limited to, measuring fluorescence intensity, measuring folding activity, measuring folding kinetics, measuring thermostability, or measuring resistance to chemical denaturation. Increased fluorescence, decreased background fluorescence and/or increase stability can be measured compared to the fluorescence of stability of the RFP prior to the directed mutagenesis or compared to an RFP having the amino acid sequence of SEQ ID NO: 4 and SEQ ID NO: 5.

In some embodiments, the destabilizing loops comprise the amino acid sequence of SEQ ID NO: 1, SEQ ID NO: 2, or SEQ ID NO: 3. In some embodiments, a destabilizing loop having the amino acid sequence of SEQ ID NO: 1 is inserted between codons coding for Gly52 and Pro53 relative to the amino acid sequence of SEQ IN NO: 4. In some embodiments, a destabilizing loop having the amino acid sequence of SEQ ID NO: 2 is inserted between codons coding for Asp101 and Gly 102 relative to the amino acid sequence of SEQ IN NO: 4. In some embodiments, a destabilizing loop having the amino acid sequence of SEQ ID NO: 3 is inserted between codons coding for Asp169 and Gly 170 relative to the amino acid sequence of SEQ IN NO: 4. In some embodiments, a destabilizing loop having the amino acid sequence of SEQ ID NO: 1 is inserted between codons coding for Gly52 and Pro53 and a destabilizing loop having the amino acid sequence of SEQ ID NO: 2 is inserted between codons coding for Asp101 and Gly 102 relative to the amino acid sequence of SEQ IN NO: 4. In some embodiments, a destabilizing loop having the amino acid sequence of SEQ ID NO: 1 is inserted between codons coding for Gly52 and Pro53 and a destabilizing loop having the amino acid sequence of SEQ ID NO: 3 is inserted between codons coding for Asp169 and Gly 170 relative to the amino acid sequence of SEQ IN NO: 4. In some embodiments, a destabilizing loop having the amino acid sequence of SEQ ID NO: 2 is inserted between codons coding for Asp 101 and Gly 102 and a destabilizing loop having the amino acid sequence of SEQ ID NO: 3 is inserted between codons coding for Asp169 and Gly 170 relative to the amino acid sequence of SEQ IN NO: 4.

In some embodiments, a first round of directed evolution comprises inserting a destabilizing loop into an RFP and performing directed evolution to identify mutants with increased fluorescence, decreased background fluorescence, or stability. In some embodiments, a first round of directed evolution comprises inserting a second destabilizing loop into one or more mutants identified in the first round of directed evolution and performing directed evolution to identify mutants with increased fluorescence, decreased background fluorescence or stability. In some embodiments, a third round of directed evolution comprises inserting a third destabilizing loop into one or more mutants identified in the second round of directed evolution and performing directed evolution to identify mutants with increased fluorescence, decreased background fluorescence or stability.

Various techniques for introducing mutations into a nucleic acid encoding a protein are well known in the art. Such methods include, but are not limited to, error-prone PCR, chemical mutagenesis, cassette mutagenesis, use of mutator host cells, recombination, oligonucleotide-directed mutagenesis, phosphorothioate-modified DNA mutagenesis, mutagenesis using uracil-containing templates, mutagenesis using gapped duplex DNA, point mismatch repair, mutagenesis using repair-deficient host strains, deletion mutagenesis, codon-based mutagenesis, DNA shuffling, and saturation mutagenesis

F. Method of Use

The described RFPs may be employed for all applications, methods and uses to which fluorescent proteins are or may be applied. Such methods include, but are not limited to, markers, protein tags, solubility screening, generation of split-fluorescent protein systems and assays, protein trafficking and localization assays, and FRET applications. For example, described improved RFPs may be coupled to antibodies, polynucleotides, or other proteins for use in detection assays such as immunoassays or hybridization assays, or to track the movement of proteins in cells. The described improved RFPs may be used in systems to detect induction of transcription.

In some embodiments, a nucleotide sequence encoding an improved RFP can be fused to a promoter or other expression control sequence of interest, which can be contained in an expression vector. The construct can be transfected into a cell, and induction of the promoter (or other regulatory element) can be measured by detecting the presence or amount of fluorescence form the improved RFP, thereby allowing a means to observe the responsiveness of a signaling pathway from receptor to promoter.

In some embodiments, the improved RFPs are used in applications of environments in which enhanced stability is required in order for the fluorescent phenotype to survive. Such applications include, but are not limited to, increased or elevated temperature (e.g., greater than 50° C., greater than 55° C., greater than 60° C., greater than 65° C., greater than 70° C., greater than 75°, or greater than 80° C.).

In some embodiments, the improved RFPs can be linked to a molecule to facilitate identifying the presence, location, or abondance of the molecule in a sample. The molecule can be, but is not limited to, a polypeptide, a polynucleotide. The polypeptide can be, but is not limited to, an antibody, an enzyme, or a receptor. The sample can, but is not limited to, a biological sample or an environmental sample. The biological sample can be, but is not limited to, a cell, a tissue, or an animal, or a sample derived from a cell, a tissue, or an animal. An improved RFP may be linked to the molecule directly or indirectly, using any linkage that is stable under the conditions to which the protein-molecule complex is to be exposed. An improved RFP and the molecule can be linked via a chemical reaction between reactive groups present on the RFP and molecule, or the linkage can be mediated by linker moiety. Where the molecule is a polypeptide, improved RFP and the polypeptide may be formed as a fusion protein encoded by a nucleic acid.

SEQUENCES

The nucleotide and amino acid sequences listed in the accompanying sequence listing are shown using standard letter abbreviations for nucleotide bases, and one code for amino acids. The nucleotide sequences follow the standard convention of beginning at the 5' end of the sequence and proceeding forward (i.e., from left to right in each line) to the 3' end. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus. It is understood that a description of an amino acid sequence includes a description of a nucleic acid sequence encoding the amino acid sequence.

```
SEQ ID NO: 1: sfCherry destabilizing loop 1
SRERDYRLDYTR

SEQ ID NO: 2: sfCherry destabilizing loop 2
LKQHFWSTPRTTS

SEQ ID NO: 3: sfCherry destabilizing loop 3
IRNLKYTN

Cherry (SEQ ID NO: 4): red fluorescent protein (RFP) Cherry amino acid
sequence
EEDNMAIIKEFMRFKVHMEGSVNGHEFEIEGEGEGRPYEGTQTAKLKVTKGGPLPFAWDILSPQFMYGSK
AYVKHPADIPDYLKLSFPEGFKWERVMNFEDGGVVTVTQDSSLQDGEFIYKVKLRGTNFPSDGPVMQKKT
NGWEASSERMYPEDGALKGEIKQRLKLKDGGHYDAEVKTTYKAKKPVQLPGAYNVNIKLDITSHNEDYTI
VEQYERAEGRHSTGG
```

-continued

--- sfCherry(SEQ ID NO: 5) RFP sfCherry amino acid sequence
EEDNMAIIKEFMRFKVHMEGSVNGHEFEIEGEGEGHPYEGTQTAKLKVTKGGPLPFAWDILSPQFMYGSK
AYVKHPADIPDYLKLSFPEGFTWERVMNFEDGGVVTVTQDSSLQDGEFIYKVKLLGTNFPSDGPVMQKKT
NGWEASTERMYPEDGALKGEINQRLKLKDGGHYDAEVKTTYKAKKPVQLPGAYNVDIKLDITSHNEDYTI
VEQYERAEGRHSTGG Cherry-loop1 (SEQ ID NO: 6) RFP Cherry amino acid sequence with
destabilizing loop 1 inserted between amino acids G52 and P53

EEDNMAIIKEFMRFKVHMEGSVNGHEFEIEGEGEGRPYEGTQTAKLKVTKGG[SRERDYRLDYTR]PLPFAW

DILSPQFMYGSKAYVKHPADIPDYLKLSFPEGFKWERVMNFEDGGVVTVTQDSSLQDGEFIYKVKLRGTN
FPSDGPVMQKKTNGWEASSERMYPEDGALKGEIKQRLKLKDGGHYDAEVKTTYKAKKPVQLPGAYNVNIK
LDITSHNEDYTIVEQYERAEGRHSTGG sfCherry-loop1 (SEQ ID NO: 7) RFP sfCherry amino acid sequence with
destabilizing loop 1 inserted between amino acids G52 and P53

EEDNMAIIKEFMRFKVHMEGSVNGHEFEIEGEGEGHPYEGTQTAKLKVTKGG[SRERDYRLDYTR]PLPFAW

DILSPQFMYGSKAYVKHPADIPDYLKLSFPEGFTWERVMNFEDGGVVTVTQDSSLQDGEFIYKVKLLGTN
FPSDGPVMQKKTNGWEASTERMYPEDGALKGEINQRLKLKDGGHYDAEVKTTYKAKKPVQLPGAYNVDIK
LDITSHNEDYTIVEQYERAEGRHSTGG

Cherry-loop2 (SEQ ID NO: 8) RFP Cherry amino acid sequence with
destabilizing loop 2 inserted between amino acids Asp101 and Gly102
EEDNMAIIKEFMRFKVHMEGSVNGHEFEIEGEGEGRPYEGTQTAKLKVTKGGPLPFAWDILSPQFMYGSK

AYVKHPADIPDYLKLSFPEGFKWERVMNFED[LKQHFWSTPRTTS]GGVVTVTQDSSLQDGEFIYKVKLRGT

NFPSDGPVMQKKTNGWEASSERMYPEDGALKGEIKQRLKLKDGGHYDAEVKTTYKAKKPVQLPGAYNVNI
KLDITSHNEDYTIVEQYERAEGRHSTGG sfCherry-loop2 (SEQ ID NO: 9) RFP sfCherry amino acid sequence with
destabilizing loop 2 inserted between amino acids Asp101 and Gly 102
EEDNMAIIKEFMRFKVHMEGSVNGHEFEIEGEGEGHPYEGTQTAKLKVTKGGPLPFAWDILSPQFMYGSK

AYVKHPADIPDYLKLSFPEGFTWERVMNFED[LKQHFWSTPRTTS]GGVVTVTQDSSLQDGEFIYKVKLLGT

NFPSDGPVMQKKINGWEASTERMYPEDGALKGEINQRLKLKDGGHYDAEVKTTYKAKKPVQLPGAYNVDI
KLDITSHNEDYTIVEQYERAEGRHSTGG

Cherry-loop3 (SEQ ID NO: 10) RFP Cherry amino acid sequence with
destabilizing loop 3 inserted between amino acids Asp169 and Gly 170
EEDNMAIIKEFMRFKVHMEGSVNGHEFEIEGEGEGRPYEGTQTAKLKVTKGGPLPFAWDILSPQFMYGSK
AYVKHPADIPDYLKLSFPEGFKWERVMNFEDGGVVTVTQDSSLQDGEFIYKVKLRGTNFPSDGPVMQKKT

NGWEASSERMYPEDGALKGEIKQRLKLKD[IRNLKYTN]GGHYDAEVKTTYKAKKPVQLPGAYNVNIKLDIT

SHNEDYTIVEQYERAEGRHSTGG sfCherry-loop3 (SEQ ID NO:11) RFP sfCherry amino acid sequence with
destabilizing loop 3 inserted between amino acids Asp169 and Gly170
EEDNMAIIKEFMRFKVHMEGSVNGHEFEIEGEGEGHPYEGTQTAKLKVTKGGPLPFAWDILSPQFMYGSK
AYVKHPADIPDYLKLSFPEGFTWERVMNFEDGGVVTVTQDSSLQDGEFIYKVKLLGTNFPSDGPVMQKKT

NGWEASTERMYPEDGALKGEINQRLKLKD[IRNLKYTN]GGHYDAEVKTTYKAKKPVQLPGAYNVDIKLDIT

SHNEDYTIVEQYERAEGRHSTGG

Cherry-loop1/3 (SEQ ID NO: 12) RFP Cherry amino acid sequence with
destabilizing loop 1 inserted between amino acids G52 and P53 and
destabilizing loop 3 inserted between amino acids Asp169 and Gly 170

EEDNMAIIKEFMRFKVHMEGSVNGHEFEIEGEGEGRPYEGTQTAKLKVTKGG[SRERDYRLDYTR]PLPFAW

FPSDGPVMQKKTNGWEASSERMYPEDGALKGEIKQRLKLKD[IRNLKYTN]GGHYDAEVKTTYKAKKPVQLP

FPSDGPVMQKKTNGWEASSERMYPEDGALKGEIKQRLKLKDIRNLKYTNGGHYDAEVKTTYKAKKPVQLP
GAYNVNIKLDITSHNEDYTIVEQYERAEGRHSTGG sfCherry-loop1/3 (SEQ ID NO: 13) RFP sfCherry amino acid sequence with
destabilizing loop 1 inserted between amino acids G52 and P53 and
destabilizing loop 3 inserted between amino acids Asp169 and Gly 170

EEDNMAIIKEFMRFKVHMEGSVNGHEFEIEGEGEGHPYEGTQTAKLKVTKGGSRERDYRLDYTRPLPFAW

DILSPQFMYGSKAYVKHPADIPDYLKLSFPEGFTWERVMNFEDGGVVTVTQDSSLQDGEFIYKVKLLGTN

FPSDGPVMQKKTNGWEASTERMYPEDGALKGEINQRLKLKDIRNLKYTNGGHYDAEVKTTYKAKKPVQLP

GAYNVDIKLDITSHNEDYTIVEQYERAEGRHSTGG sfCherry(a)-loop2(improved) (SEQ ID NO: 14) improved RFP (iRFP1) amino
acid sequence with destabilizing loop 2 inserted between amino acids
Asp101 and Gly102
EEDNMAIIKEFMRFKVYMEGSVNGHEFEIEGEGEGHPYEGTQTAKLKVTKGGPLPFSWDILSPQFMYGSK

AYVKHPADIPDYLKLSFPEGFTWERVMIFKDLKQHFWSTPRTTSGGVVTVTQDSSLQDGEFIYKVKLLGT

NFPGDGPIMQKKTNGWEASTERMYPEDGALKGEINQRLKLKDGGHYDAWVKTTYKAKKPVQLPGAYNVDI
KLDITTHNEDYTIVEQYERAEGRHSTGG sfCherry(a) (SEQ ID NO: 15) improved RFP (iRFP1) amino acid sequence
EEDNMAIIKEFMRFKVYMEGSVNGHEFEIEGEGEGHPYEGTQTAKLKVTKGGPLPFSWDILSPQFMYGSK
AYVKHPADIPDYLKLSFPEGFTWERVMIFKDGGVVTVTQDSSLQDGEFIYKVKLLGTNFPGDGPIMQKKT
NGWEASTERMYPEDGALKGEINQRLKLKDGGHYDAWVKTTYKAKKPVQLPGAYNVDIKLDITTHNEDYTI
VEQYERAEGRHSTGG sfCherry(b)-loop2(improved) (SEQ ID NO: 16) improved RFP (iRFP2)
amino acid sequence with destabilizing loop 2 inserted between amino
acids Asp101 and Gly102
EEDNMAIIKEFMRFKVFMEGSVNGHEFEIEGEGEGHPYEGTQTAKLKVTKGGPLPFSWDILSPQFMYGSK

AYVKHPADIPDYLKLSFPEGFTWERVMIFKDLKQHFWSTPRTTSGGVVTVTQDSSLQDGEFIYKVKLLGT

NFPGDGPIMQKKTNGWEASTERMYPEDGALKGEINQRLKLKDGGHYDAWVKTTYKAKKPVQLPGAYNVDI
KLDITTHNEDYTIVEQYERAEGRHSTGG sfCherry(b) (SEQ ID NO: 17) improved RFP (iRFP2) amino acid sequence
EEDNMAIIKEFMRFKVEMEGSVNGHEFEIEGEGEGHPYEGTQTAKLKVTKGGPLPFSWDILSPQFMYGSK
AYVKHPADIPDYLKLSFPEGFTWERVMIFKDGGVVTVTQDSSLQDGEFIYKVKLLGTNFPGDGPIMQKKT
NGWEASTERMYPEDGALKGEINQRLKLKDGGHYDAWVKTTYKAKKPVQLPGAYNVDIKLDITTHNEDYTI
VEQYERAEGRHSTGG sfCherry(c)-loop 1/3(improved) (SEQ ID NO: 18) improved RFP (iRFP3)
amino acid sequence with destabilizing loop 1 inserted between amino
acids G52 and P53 and destabilizing loop 3 inserted between amino acids
Asp169 and Gly 170

EENNMAIIKEFMRFKVHMEGSVNGYEFEIEGEGERYPYEGTQTARLKVTKGGSRERDYRLDYTRPLPFAW

DILSPQFMYGSKAYVKHPADIPDYFKLSFPEGFTWERVMNFEDGGVVTVTQDSSLHNGEFIYKVKLLGTN

FPSDGPVMQKRTNGWEASTERMYPEDGALKGEINQRLKLKDIRNLKYTNGGHYHAHVKTIYKAKKPVQLP

GAYNVDIKLDITSHNEDYTIVEQYERAEARHSTGG sfCherry(c) (SEQ ID NO: 19) improved RFP (iRFP3) amino acid sequence
EENNMAIIKEFMRFKVHMEGSVNGYEFEIEGEGERYPYEGTQTARLKVTKGGPLPFAWDILSPQFMYGSK
AYVKHPADIPDYFKLSFPEGFTWERVMNFEDGGVVTVTQDSSLHNGEFIYKVKLLGTNFPSDGPVMQKRT
NGWEASTERMYPEDGALKGEINQRLKLKDGGHYHAHVKTIYKAKKPVQLPGAYNVDIKLDITSHNEDYTI
VEQYERAEARHSTGG sfCherry-loop2 N98I + E100K + E176W + S131G + V135I (SEQ ID NO: 20)
improved RFB nucleic acid sequence containing a sequence encoding a
destabilizing loop 2 insertion between codons encoding amino acids
Asp101 and Gly102
gaggaggataacatggcaattatcaaggaatttatgcgatttaaggttcacatggaggggttctgttaatg
gacacgaatttgagatcgaaggagagggtgaaggtcatccttacgagggaacacagaccgctaaattgaa
agtcactaaaggaggacctcttccattcgcctgggatatactttcccctcagtttatgtatggttctaaa
gcctatgtcaaacatccggctgacatcccagactatttgaagttgtccttccccgaaggttttacatggg
aacgcgttatgattttcaaggatcttaagcaacattttttggagtactcctcgaacgacatcgggcggggt
cgtcacggtgacacaggactccagcttgcaagatggtgagtttatttataaagtcaagttattaggtact -continued

```
aattttccaggggatggacccattatgcagaaaaagacgatgggctgggaggcatccactgaacgcatgt
acccagaagacggtgcactcaaaggtgagatcaatcaacgcctcaagcttaaagatggtggccattacga
tgcatgggttaagacaacatataaggcaaaaaagcctgtccagttaccaggcgcctataacgtggacata
aaattggacattacgagccataacgaggactacacaatcgtggagcagtatgagcgtgcagagggtcgtc
acagtacaggtggc
```

Various aspects of the invention are further described and illustrated by way of the several examples which follow, none of which are intended to limit the scope of the invention.

EXAMPLES

Example 1. Destabilization Loops Inserted into Superfolder Cherry

Nucleic acid sequences encoding three different loops were inserted into the coding sequence of Superfolder Cherry (sfCherry, as disclosed in Nature Biotech Dec. 22, 2004; (12): 1567-72) with 6 amino acid substitutions: R36H, K92T, R125L, S147T, K162N, N196D. Loop1 ("CDRH3 binding": SRERDYRLDYTR; SEQ ID NO: 1) was inserted between codons coding for Gly52 and Pro53. Loop 2 ("CDRL3 binding": LKQHFWSTPRTTS; SEQ ID NO: 2) was inserted between codons coding for Asp101 and Gly 102. Loop3 ("Streptavidin binding": IRNLKYTN; SEQ ID NO: 3) was inserted between codons coding for Asp169 and Gly170.

The insertion of loop 1 alone or loop 3 alone had minimal effect on protein stability. The combination of loop 1 and loop 3, sfCherry-loop1/3. had strong effect on protein stability. Insertion of loop 2 alone (sfCherry-loop2) had a significant effect on fluorescence intensity of sfCherry. Fluorescence intensity of sfCherry-loop2 was faint even when the protein was expressed at low temperature for several hours.

Example 2. Directed Evolution of sfCherry-Loop2 Using DNA Shuffling

A. Round 1: Directed evolution of sfCherry-loop2 in pETN6His was performed using DNA shuffling. The directed evolution was performed at 34° C. From about 20,000 clones, the 96 brightest clones were selected and analyzed. The selected sfCherry variants contained the following mutations: H17Y, N98K, E100G, S131L, V135I, E176K, S203T. Most clones contained only one beneficial mutation. One variant contained two substitutions: E98K and S203T.

B. Round 2: Directed evolution was performed at 34° C., recombining the top about 25 brightest variants from round 1 that contained a unique beneficial mutation. The brightest variants were again selected and analyzed. The brightest clones were found to contain combinations of mutations detected from the first round along with 1 new mutation identified, A57S. 4 variants of particular interest were identified. These variants had the following amino acid substitutions:
Variant 1: H17Y, N98K, V135I, E176K;
Variant 2: N98K, S131L, E176K;
Variant 3: N98K, E100G, V135I; and
Variant 4: A57S, N98K.

C. Round 3: Directed evolution was performed at 37° C. using the top about 25 brightest variants from round 2 that contained unique beneficial mutations (FIG. 1). No new mutation identified in round 3. Three variants were selected. These variants had the following amino acid substitutions:
Variant 1: H17Y, A57S, N98K, S131L, V135I, E176K;
Variant 2: H17Y, A57S, N98K, V135I, E176K; and
Variant 3: A57S, N98K, V135I, E176K.

Little improvement was noted in round 3 relative to round 2. The round 3 variants were still faint compared to sfCherry without the loop 2 insertion. No additional mutations were identified in further rounds.

Example 3. Directed Evolution of sfCherry-Loop2 Using Saturation Mutagenesis

Directed evolution of sfCherry-loop2 in pETN6His was performed using saturation mutagenesis.

A. Identification the hotspots (sites of beneficial mutations). Saturation mutagenesis was performed using all 8 mutations identified from the first and second rounds for DNA shuffling mutagenesis of sfCherry-loop2: H17Y, A57S, N98K, E100G, S131L, V135I, E176K, and S203T. For each of these eight sights, all possibilities were analyzed using degeneracy primers NNK which covers all 20 amino acids with 32 codons including 1 stop codon.

B. Ranking the sites. 7 degeneracy libraries for H17, A57, N98+E100, V135, E176, S203, S131 (N98+E100 were together on one clone) were constructed. Resulting clones were plated out and ranked based on the brightest mutant of each site N98+E100>E176>S131, V135>H17>A57>S203. This means, for example, that the brightest clones in the NNK library of N98+E110 were brighter than the brightest clones of NNK library of E176, and so on. These 7 sublibraries are ranked in decreasing order based on the brightest members of the library.

C. Sequential optimization. Saturation mutagenesis of N98+E100 was performed first. The brightest variants (best fluorescence) were identified and sequenced. N98I+E100K was identified as the best variant from the N98NNK E100NNK library. Next, saturation mutagenesis were performed at the E176 position. After analyzing fluorescent intensity, N98I+E100K+E176W as selected as the best (brightest) variant. Third, saturation mutagenesis were performed at the S131 site. After analyzing fluorescent intensity, N98I+E100K+ E176W+S131G+V135I. (V135I mutation spontaneously appeared) as selected as the best (brightest) variant. The S131G was found to promote faster protein folding. 6 bright clones: F1, H1, C2, D2, G5, F7 each had the N98I+E100K+E176W+S131G+V135I amino acid substitutions. This variant was brighter than the best variants from the 3rd round directed evolution of sfCherry-loop-2        (H17Y+A57S+N98K+S131L+ V135I+E176K)

The sequence of this sfCherry-loop2 N98I+E100K+ E176W+S131G+V135I variant is SEQ ID NO: 20, which sequence includes the loop 2 insertion between amino acids 101 and 102.

Figure 2:
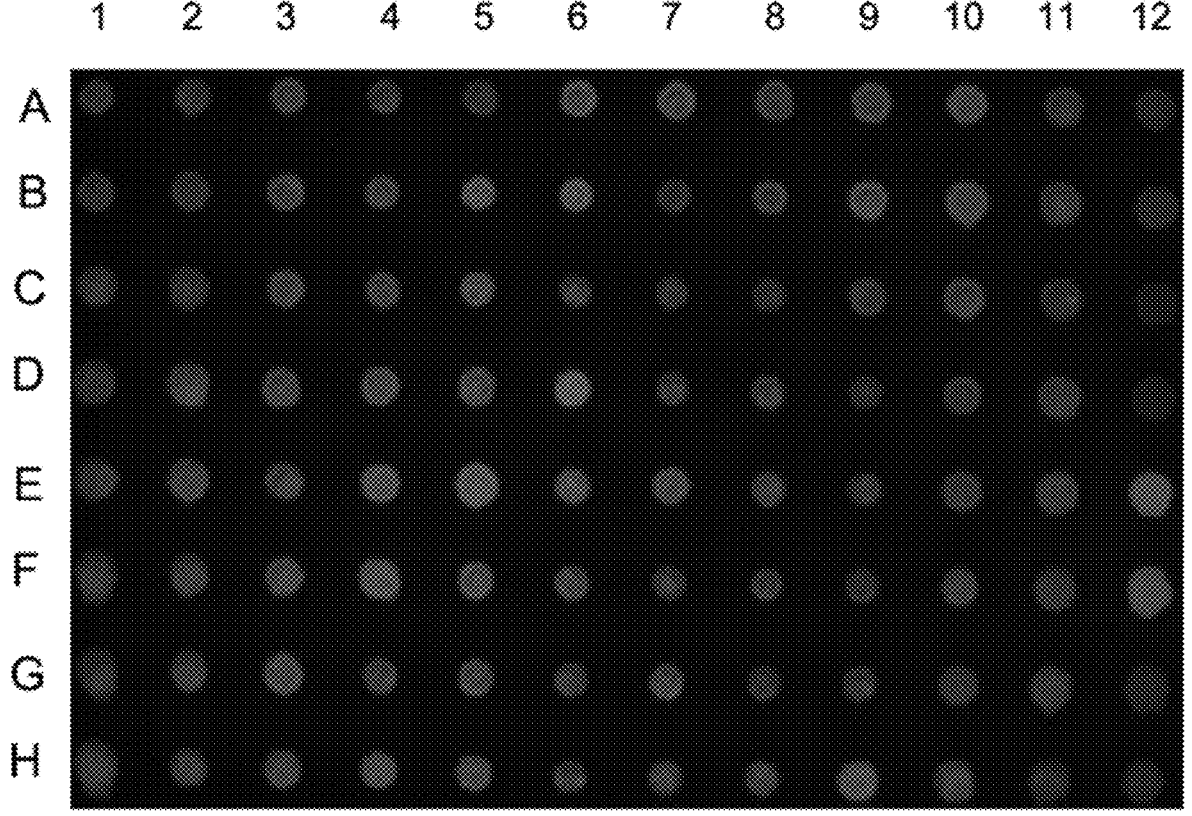
FIG. 2. Image illustrating directed evolution of sfCherry-loop2 N98I+E100K+E176W+S131G+V135I+H17NNK. Rows A and B: Cherry loop 2 N98I+E100K+E176W+S131G+V135I+H17NNK. Rows C and D: sfCherry-loop 2 best of third round. Rows E and F: sfCherry without loop. Rows G and H: sfCherry-loop2 N98I+E100K+E176W+S131G+V135I.

One clone was selected and saturation mutagenesis at H17 was performed. Proteins were expressed at 37° C. for 1 hour 30 minutes. Variants were observed that were almost as bright as the parent sfCherry (i.e., without any loop) (FIG. 2). Two variants were selected:

(a)  H17Y+N98I+E100K+E176W+S131G+V135I (sfCherry (a)) and
(b)  H17F+N98I+E100K+E176W+S131G+V135I (sfCherry (b)).

These two variants had similar improved fluorescence.

Example 4. Directed Evolution of SF Cherry Loop 1+3

Directed evolution of sfCherry-loop1/3 in pETN6His was performed using DNA shuffling and random mutagenesis.

A. Round 1. The directed evolution was performed at 34° C. Seven mutations that improved fluorescence were identified: D3N, H25Y, H36Y, K45R, D115N, K139R, E176K. One variant was identified that had mutations at two of these positions: K139R and E176K.

Figure 3:
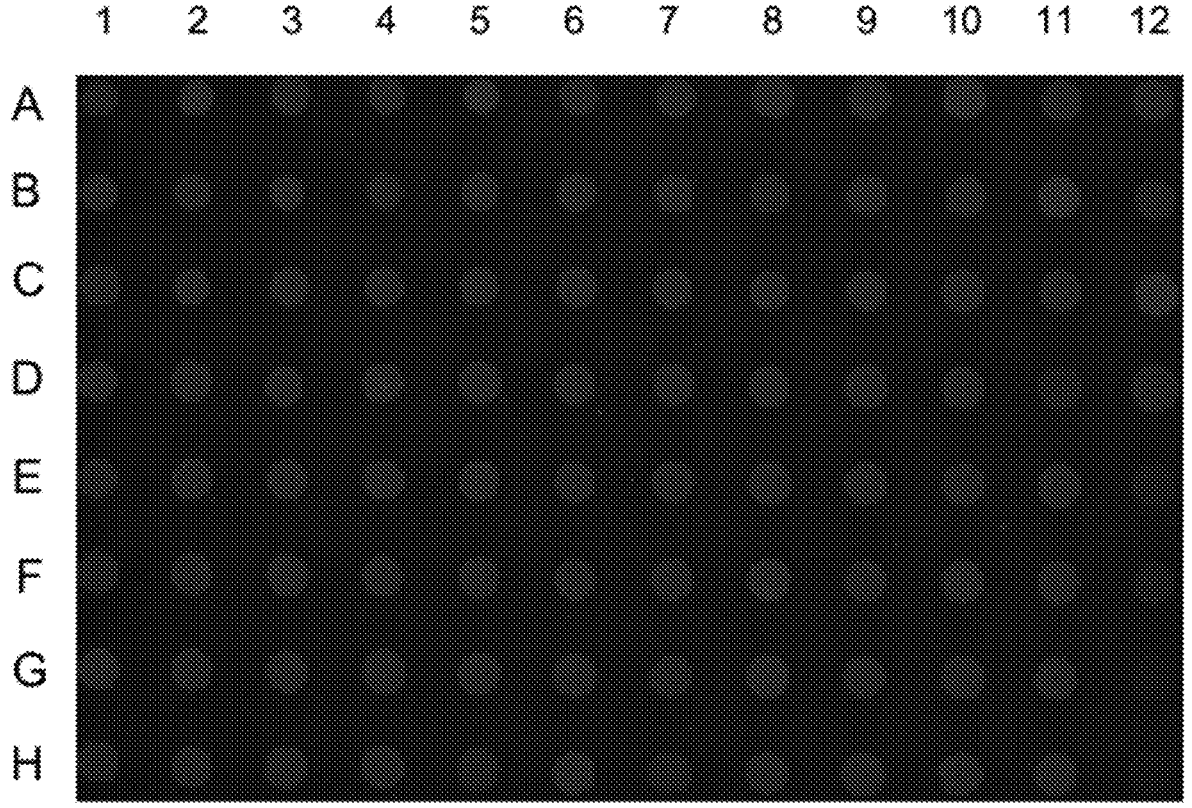
FIG. 3. Image illustrating directed evolution of sfCherry-loop1/3. Rows A-D: sfCherry-loop1/3 second round directed evolution. Rows E and F: sfCherry-loop1/3 best of first round. Rows G and H: sfCherry-loop1/3.

B. Round 2. Directed evolution (DNA shuffling) was performed at 34° C. (FIG. 3). In round 2, no mutations that improved fluorescence were identified at any new sites not identified in round 1. 4 variants of particular interest were identified. These variants had the following amino acid substitutions:
Variant 1: D3N, H25Y, K139R;
Variant 2: H25Y, K45R, K139R;
Variant 3: H25Y, D115N, K139R; and
Variant 4: H25Y, H36Y.

C. Round 3. Directed evolution was performed at 34° C. and 37° C. Following round 3, two variants were selected. These variants had the following amino acid substitutions:
Variant 1: D3N, H25Y, H36Y, K45R, K139R; and
Variant 2: D3N, H25Y, H36Y, D115N, K139R.

These variants were faint compared to the parent sfCherry (i.e., without loop 1 and loop 3 insertions).

Example 5. Directed Evolution of sfCherry-Loop1/3 Using Saturation Mutagenesis Directed evolution of sfCherry-loop1/3 in pETN6His was performed using saturation mutagenesis.

A. Identification the hotspots (sites of beneficial mutations). Saturation mutagenesis was performed using all y mutations identified from the first and second rounds for DNA shuffling mutagenesis of sfCherry-loop1/3: D3, H25, H36, K45, D115, K139, and E176. For each of these seven sights, all possibilities were analyzed using degeneracy primers NNK which covers all 20 amino acids with 32 codons including 1 stop codon.

B. Ranking the sites. 7 degeneracy libraries for D3, H25, H36, K45, D115, K139, and E176 were constructed. Resulting clones were plated out and ranked based on the brightest mutant of each site: H25>K139>E196>H36>K45>D127>D3.

Figure 4:
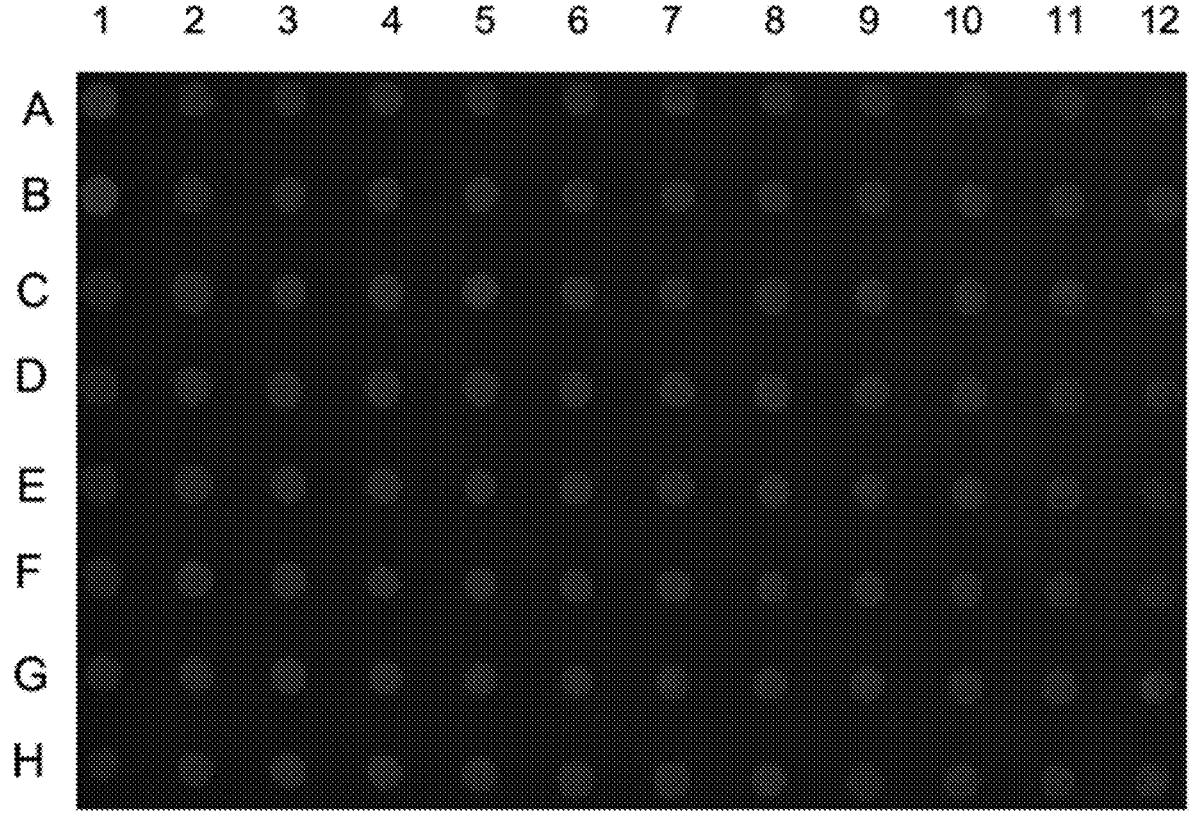
FIG. 4. Image illustrating directed evolution of sfCherry-loop 1/3 H25Y+K139R+E176NNK. Rows A and B: sfCherry-loop1/3 H25Y+K139R+E176NNK. Rows C and D. sfCherry-loop1/3 best of second round. Rows E and F: sfCherry-loop 1/3 H25Y+K139R. Rows G and H: sfCherry-loop 1/3 best of third round.
Figure 5:
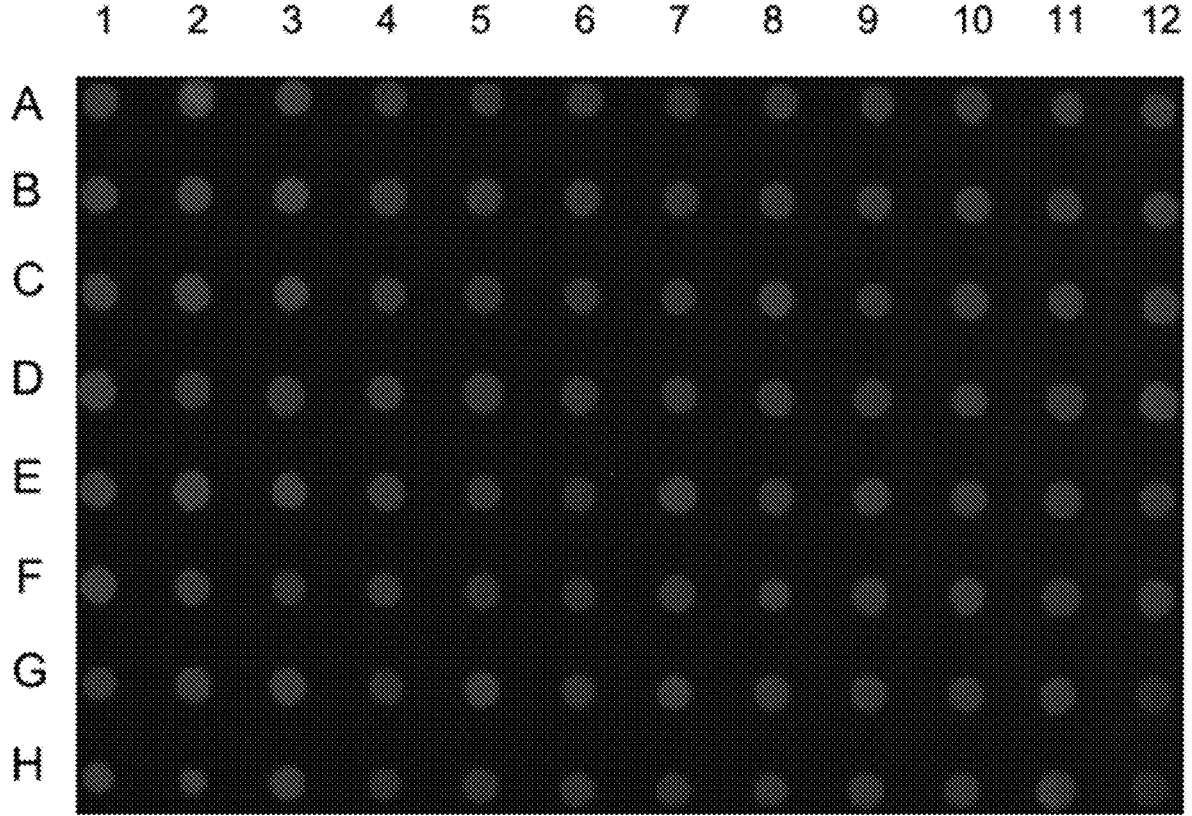
FIG. 5. Image illustrating directed evolution of sfCherry-loop1/3 H25Y+K139R+D174H+E176H+H36NNK. Rows A to D: sfCherry-loop 1/3 H25Y+K139R+D174H+E176H+H36NNK. Rows E and F: sfCherry-loop1/3 H25Y+K139R+D174H+E176H. Rows G and H: sfCherry-loop1/3 best of third round.
Figure 6:
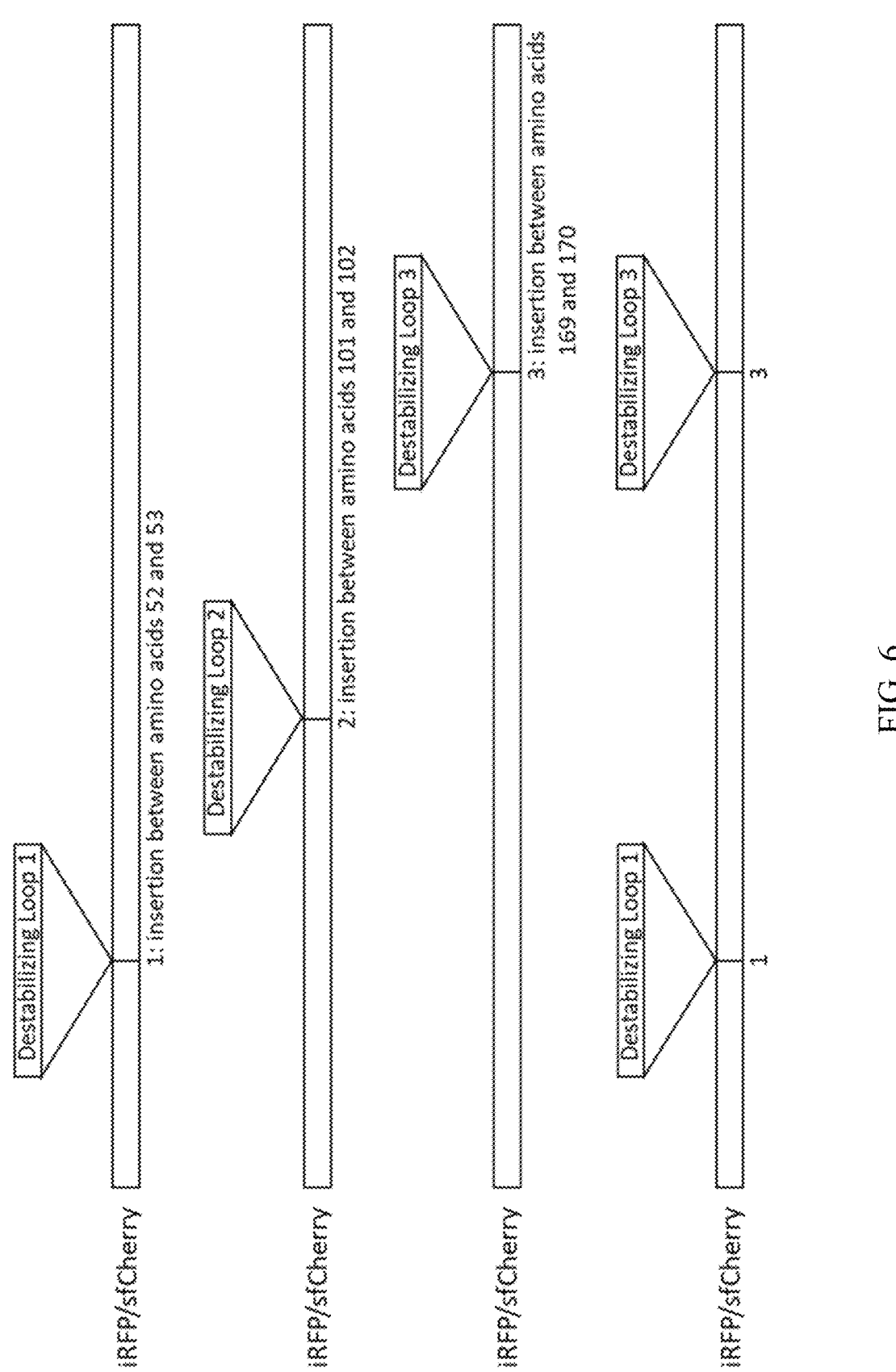
FIG. 6. Diagram illustrating exemplary insertions of destabilizing loops into sfCherry or an improved RFD (iRFD). Nucleic acids encoding the constructs can be used to generate improved RFPs.

C. Sequential optimization. Saturation mutagenesis of H25 was performed first. From this mutagenesis, H25Y was selected. The variant was then subjected to saturation mutagenesis at the K139 position. From this mutagenesis, H25Y+K139R was selected. This variant was then subjected to saturation mutagenesis at the E176 site (FIG. 4). Form this mutagenesis, H25Y+K139R+D174H+E176H was selected. This variant was then subjected to saturation mutagenesis at the H36 site. Form this mutagenesis, H25Y+K139R+D174H+E176H+H36Y and H25Y+K139R+D174H+E176H+H36R were selected (FIG. 5). These variants were then subjected to saturation mutagenesis at the K45 site. Form this mutagenesis, H25Y+K139R+D174H+E176H+H36Y+K45R was selected. This variant was similar to mutations found from DNA shuffling. While brighter than the variants identified from the DNA shuffling mutagenesis, this variant was not a bright as the parent sfCherry.

D. The H25Y+H36Y+K45R+K139R+D174H+E176H protein (sfCherry (c)) is then made by removing loop 1 and loop 3. The loops are removed from the nucleic acid sequence using methods available in the art. An expression vector encoding SEQ ID NO: 18 is then used to produce the improved sfCherry protein.

E. SfCherry-loop1/3 or sfCherry (c)-loop1/3 is subjected to additional rounds of directed mutagenesis using DNA shuffling or saturation mutagenesis, yielding more mutations including L83F, Q114H, T180I, G219A.

Example 6. Constructs for Use in Directed Evolution of Improved Red Fluorescent Proteins Mutations identified as increasing stability or fluorescence from the directed mutagenesis of the sfCherry-loop2 construct can be combined with the mutations identified as increasing stability or fluorescence from the directed mutagenesis of the sfCherry-loop1/3 construct to generation an RFD resistant to all 3 loop insertions.

The invention claimed is:

1. A red fluorescent protein comprising an amino acid sequence having at least 97% sequence identity to
   (a) SEQ ID NO: 15, wherein amino acid 17 is tyrosine, amino acid 57 is serine, amino acid 98 is isoleucine, amino acid 100 is lysine, amino acid 131 is glycine, amino acid 135 is isoleucine, amino acid 176 is tryptophan, and amino acid 203 is threonine;
   (b) SEQ ID NO: 17 wherein amino acid 17 is phenylalanine, amino acid 57 is serine, amino acid 98 is isoleucine, amino acid 100 is lysine, amino acid 131 is glutamate, amino acid 135 is isoleucine; amino acid 176 is tryptophan, and amino acid 203 is asparagine; or
   (c) SEQ ID NO: 19, wherein amino acid 3 is asparagine, amino acid 25 is tyrosine, amino acid 36 is tyrosine, amino acid 45 is arginine, amino acid 83 is phenylalanine, amino acid 114 is histidine, amino acid 115 is asparagine, amino acid 139 is arginine, amino acid 174 is histidine, amino acid is 176 is histidine, amino acid 180 is isoleucine, and amino acid 219 is alanine.

2. The red fluorescent protein of claim 1, wherein the red fluorescent protein comprises an amino acid sequence having at least 97% sequence identity to the amino acid sequence of:
   (a) SEQ ID NO: 15, wherein amino acid 17 is tyrosine, amino acid 57 is serine, amino acid 98 is isoleucine, amino acid 100 is lysine, amino acid 131 is glycine, amino acid 135 is isoleucine, amino acid 176 is tryptophan, amino acid 203 is threonine, amino acid 36 is histidine, amino acid 92 is threonine, amino acid 125 is leucine, amino acid 147 is threonine, amino acid 162 is asparagine, and amino acid 196 is aspartate;
   (b) SEQ ID NO: 17 wherein amino acid 17 is phenylalanine, amino acid 57 is serine, amino acid 98 is isoleucine, amino acid 100 is lysine, amino acid 131 is glutamate, amino acid 135 is isoleucine; amino acid 176 is tryptophan, amino acid 203 is asparagine, amino acid 36 is histidine, amino acid 92 is threonine, amino acid 125 is leucine, amino acid 147 is threonine, amino acid 162 is asparagine, and amino acid 196 is aspartate; or (c) SEQ ID NO: 19, wherein amino acid 3 is asparagine, amino acid 25 is tyrosine, amino acid 36 is tyrosine, amino acid 45 is arginine, amino acid 83 is phenylalanine, amino acid 114 is histidine, amino acid 115 is asparagine, amino acid 139 is arginine, amino acid 174 is histidine, amino acid is 176 is histidine, amino acid 180 is isoleucine, amino acid 219 is alanine, amino acid 92 is threonine, amino acid 125 is leucine, amino acid 147 is threonine, amino acid 162 is asparagine, and amino acid 196 is aspartate.

3. The red fluorescent protein of claim 2, wherein the red fluorescent protein comprises the amino acid sequence of SEQ ID NO: 15, SEQ ID NO: 17, or SEQ ID NO: 19, and wherein said sequences possess the amino acids as in (a), (b) and (c), respectively.

4. The red fluorescent protein of claim 2, wherein the amino acid sequence of the red fluorescent protein consists of the amino acid sequence of SEQ ID NO: 15, SEQ ID NO: 17, or SEQ ID NO: 19, and wherein said sequences possess the amino acids as in (a), (b) and (c), respectively.

5. The red fluorescent protein of claim 3, wherein the red fluorescent protein further comprises a fusion protein.

6. A nucleic acid encoding the red fluorescent protein of claim 1.

7. The nucleic acid of claim 6, wherein the nucleic acid is provided in a CRISPR construct.

8. A host cell comprising the nucleic acid of claim 6.

* * * * *

SEQUENCE LISTING

```
Sequence total quantity: 20
SEQ ID NO: 1          moltype = AA  length = 12
FEATURE               Location/Qualifiers
source                1..12
                      mol_type = protein
                      organism = synthetic construct
SEQUENCE: 1
SRERDYRLDY TR                                              12

SEQ ID NO: 2          moltype = AA  length = 13
FEATURE               Location/Qualifiers
```

-continued

```
source                   1..13
                         mol_type = protein
                         organism = synthetic construct
SEQUENCE: 2
LKQHFWSTPR TTS                                                          13

SEQ ID NO: 3             moltype = AA   length = 8
FEATURE                  Location/Qualifiers
source                   1..8
                         mol_type = protein
                         organism = synthetic construct
SEQUENCE: 3
IRNLKYTN                                                                8

SEQ ID NO: 4             moltype = AA   length = 225
FEATURE                  Location/Qualifiers
source                   1..225
                         mol_type = protein
                         organism = synthetic construct
SEQUENCE: 4
EEDNMAIIKE FMRFKVHMEG SVNGHEFEIE GEGEGRPYEG TQTAKLKVTK GGPLPFAWDI       60
LSPQFMYGSK AYVKHPADIP DYLKLSFPEG FKWERVMNFE DGGVVTVTQD SSLQDGEFIY       120
KVKLRGTNFP SDGPVMQKKT NGWEASSERM YPEDGALKGE IKQRLKLKDG GHYDAEVKTT       180
YKAKKPVQLP GAYNVNIKLD ITSHNEDYTI VEQYERAEGR HSTGG                       225

SEQ ID NO: 5             moltype = AA   length = 225
FEATURE                  Location/Qualifiers
source                   1..225
                         mol_type = protein
                         organism = synthetic construct
SEQUENCE: 5
EEDNMAIIKE FMRFKVHMEG SVNGHEFEIE GEGEGHPYEG TQTAKLKVTK GGPLPFAWDI       60
LSPQFMYGSK AYVKHPADIP DYLKLSFPEG FTWERVMNFE DGGVVTVTQD SSLQDGEFIY       120
KVKLLGTNFP SDGPVMQKKT NGWEASTERM YPEDGALKGE INQRLKLKDG GHYDAEVKTT       180
YKAKKPVQLP GAYNVDIKLD ITSHNEDYTI VEQYERAEGR HSTGG                       225

SEQ ID NO: 6             moltype = AA   length = 237
FEATURE                  Location/Qualifiers
source                   1..237
                         mol_type = protein
                         organism = synthetic construct
SEQUENCE: 6
EEDNMAIIKE FMRFKVHMEG SVNGHEFEIE GEGEGRPYEG TQTAKLKVTK GGSRERDYRL       60
DYTRPLPFAW DILSPQFMYG SKAYVKHPAD IPDYLKLSFP EGFKWERVMN FEDGGVVTVT       120
QDSSLQDGEF IYKVKLRGTN FPSDGPVMQK KTNGWEASSE RMYPEDGALK GEIKQRLKLK       180
DGGHYDAEVK TTYKAKKPVQ LPGAYNVNIK LDITSHNEDY TIVEQYERAE GRHSTGG          237

SEQ ID NO: 7             moltype = AA   length = 237
FEATURE                  Location/Qualifiers
source                   1..237
                         mol_type = protein
                         organism = synthetic construct
SEQUENCE: 7
EEDNMAIIKE FMRFKVHMEG SVNGHEFEIE GEGEGHPYEG TQTAKLKVTK GGSRERDYRL       60
DYTRPLPFAW DILSPQFMYG SKAYVKHPAD IPDYLKLSFP EGFTWERVMN FEDGGVVTVT       120
QDSSLQDGEF IYKVKLLGTN FPSDGPVMQK KTNGWEASTE RMYPEDGALK GEINQRLKLK       180
DGGHYDAEVK TTYKAKKPVQ LPGAYNVDIK LDITSHNEDY TIVEQYERAE GRHSTGG          237

SEQ ID NO: 8             moltype = AA   length = 238
FEATURE                  Location/Qualifiers
source                   1..238
                         mol_type = protein
                         organism = synthetic construct
SEQUENCE: 8
EEDNMAIIKE FMRFKVHMEG SVNGHEFEIE GEGEGRPYEG TQTAKLKVTK GGPLPFAWDI       60
LSPQFMYGSK AYVKHPADIP DYLKLSFPEG FKWERVMNFE DLKQHFWSTP RTTSGGVVTV       120
TQDSSLQDGE FIYKVKLRGT NFPSDGPVMQ KKTNGWEASS ERMYPEDGAL KGEIKQRLKL       180
KDGGHYDAEV KTTYKAKKPV QLPGAYNVNI KLDITSHNED YTIVEQYERA EGRHSTGG         238

SEQ ID NO: 9             moltype = AA   length = 238
FEATURE                  Location/Qualifiers
source                   1..238
                         mol_type = protein
                         organism = synthetic construct
SEQUENCE: 9
EEDNMAIIKE FMRFKVHMEG SVNGHEFEIE GEGEGHPYEG TQTAKLKVTK GGPLPFAWDI       60
LSPQFMYGSK AYVKHPADIP DYLKLSFPEG FTWERVMNFE DLKQHFWSTP RTTSGGVVTV       120
TQDSSLQDGE FIYKVKLLGT NFPSDGPVMQ KKTNGWEAST ERMYPEDGAL KGEINQRLKL       180
KDGGHYDAEV KTTYKAKKPV QLPGAYNVDI KLDITSHNED YTIVEQYERA EGRHSTGG         238
```

-continued

```
SEQ ID NO: 10            moltype = AA   length = 233
FEATURE                  Location/Qualifiers
source                   1..233
                         mol_type = protein
                         organism = synthetic construct
SEQUENCE: 10
EEDNMAIIKE FMRFKVHMEG SVNGHEFEIE GEGEGRPYEG TQTAKLKVTK GGPLPFAWDI   60
LSPQFMYGSK AYVKHPADIP DYLKLSFPEG FKWERVMNFE DGGVVTVTQD SSLQDGEFIY  120
KVKLRGTNFP SDGPVMQKKT NGWEASSERM YPEDGALKGE IKQRLKLKDI RNLKYTNGGH  180
YDAEVKTTYK AKKPVQLPGA YNVNIKLDIT SHNEDYTIVE QYERAEGRHS TGG         233

SEQ ID NO: 11            moltype = AA   length = 233
FEATURE                  Location/Qualifiers
source                   1..233
                         mol_type = protein
                         organism = synthetic construct
SEQUENCE: 11
EEDNMAIIKE FMRFKVHMEG SVNGHEFEIE GEGEGHPYEG TQTAKLKVTK GGPLPFAWDI   60
LSPQFMYGSK AYVKHPADIP DYLKLSFPEG FTWERVMNFE DGGVVTVTQD SSLQDGEFIY  120
KVKLLGTNFP SDGPVMQKKT NGWEASTERM YPEDGALKGE INQRLKLKDI RNLKYTNGGH  180
YDAEVKTTYK AKKPVQLPGA YNVDIKLDIT SHNEDYTIVE QYERAEGRHS TGG         233

SEQ ID NO: 12            moltype = AA   length = 245
FEATURE                  Location/Qualifiers
source                   1..245
                         mol_type = protein
                         organism = synthetic construct
SEQUENCE: 12
EEDNMAIIKE FMRFKVHMEG SVNGHEFEIE GEGEGRPYEG TQTAKLKVTK GGSRERDYRL   60
DYTRPLPFAW DILSPQFMYG SKAYVKHPAD IPDYLKLSFP EGFKWERVMN FEDGGVVTVT  120
QDSSLQDGEF IYKVKLRGTN FPSDGPVMQK KTNGWEASSE RMYPEDGALK GEIKQRLKLK  180
DIRNLKYTNG GHYDAEVKTT YKAKKPVQLP GAYNVNIKLD ITSHNEDYTI VEQYERAEGR  240
HSTGG                                                              245

SEQ ID NO: 13            moltype = AA   length = 245
FEATURE                  Location/Qualifiers
source                   1..245
                         mol_type = protein
                         organism = synthetic construct
SEQUENCE: 13
EEDNMAIIKE FMRFKVHMEG SVNGHEFEIE GEGEGHPYEG TQTAKLKVTK GGSRERDYRL   60
DYTRPLPFAW DILSPQFMYG SKAYVKHPAD IPDYLKLSFP EGFTWERVMN FEDGGVVTVT  120
QDSSLQDGEF IYKVKLLGTN FPSDGPVMQK KTNGWEASTE RMYPEDGALK GEINQRLKLK  180
DIRNLKYTNG GHYDAEVKTT YKAKKPVQLP GAYNVDIKLD ITSHNEDYTI VEQYERAEGR  240
HSTGG                                                              245

SEQ ID NO: 14            moltype = AA   length = 238
FEATURE                  Location/Qualifiers
source                   1..238
                         mol_type = protein
                         organism = synthetic construct
SEQUENCE: 14
EEDNMAIIKE FMRFKVYMEG SVNGHEFEIE GEGEGHPYEG TQTAKLKVTK GGPLPFSWDI   60
LSPQFMYGSK AYVKHPADIP DYLKLSFPEG FTWERVMIFK DLKQHFWSTP RTTSGGVVTV  120
TQDSSLQDGE FIYKVKLLGT NFPGDGPIMQ KKTNGWEAST ERMYPEDGAL KGEINQRLKL  180
KDGGHYDAWV KTTYKAKKPV QLPGAYNVDI KLDITTHNED YTIVEQYERA EGRHSTGG    238

SEQ ID NO: 15            moltype = AA   length = 225
FEATURE                  Location/Qualifiers
source                   1..225
                         mol_type = protein
                         organism = synthetic construct
SEQUENCE: 15
EEDNMAIIKE FMRFKVYMEG SVNGHEFEIE GEGEGHPYEG TQTAKLKVTK GGPLPFSWDI   60
LSPQFMYGSK AYVKHPADIP DYLKLSFPEG FTWERVMIFK DGGVVTVTQD SSLQDGEFIY  120
KVKLLGTNFP GDGPIMQKKT NGWEASTERM YPEDGALKGE INQRLKLKDG GHYDAWVKTT  180
YKAKKPVQLP GAYNVDIKLD ITTHNEDYTI VEQYERAEGR HSTGG                 225

SEQ ID NO: 16            moltype = AA   length = 238
FEATURE                  Location/Qualifiers
source                   1..238
                         mol_type = protein
                         organism = synthetic construct
SEQUENCE: 16
EEDNMAIIKE FMRFKVFMEG SVNGHEFEIE GEGEGHPYEG TQTAKLKVTK GGPLPFSWDI   60
LSPQFMYGSK AYVKHPADIP DYLKLSFPEG FTWERVMIFK DLKQHFWSTP RTTSGGVVTV  120
TQDSSLQDGE FIYKVKLLGT NFPGDGPIMQ KKTNGWEAST ERMYPEDGAL KGEINQRLKL  180
KDGGHYDAWV KTTYKAKKPV QLPGAYNVDI KLDITTHNED YTIVEQYERA EGRHSTGG    238
```

-continued

```
SEQ ID NO: 17            moltype = AA  length = 225
FEATURE                  Location/Qualifiers
source                   1..225
                         mol_type = protein
                         organism = synthetic construct
SEQUENCE: 17
EEDNMAIIKE FMRFKVFMEG SVNGHEFEIE GEGEGHPYEG TQTAKLKVTK GGPLPFSWDI   60
LSPQFMYGSK AYVKHPADIP DYLKLSFPEG FTWERVMIFK DGGVVTVTQD SSLQDGEFIY  120
KVKLLGTNFP GDGPIMQKKT NGWEASTERM YPEDGALKGE INQRLKLKDG GHYDAWVKTT  180
YKAKKPVQLP GAYNVDIKLD ITTHNEDYTI VEQYERAEGR HSTGG               225

SEQ ID NO: 18            moltype = AA  length = 245
FEATURE                  Location/Qualifiers
source                   1..245
                         mol_type = protein
                         organism = synthetic construct
SEQUENCE: 18
EENNMAIIKE FMRFKVHMEG SVNGYEFEIE GEGERYPYEG TQTARLKVTK GGSRERDYRL   60
DYTRPLPFAW DILSPQFMYG SKAYVKHPAD IPDYFKLSFP EGFTWERVMN FEDGGVVTVT  120
QDSSLHNGEF IYKVKLLGTN FPSDGPVMQK RTNGWEASTE RMYPEDGALK GEINQRLKLK  180
DIRNLKYTNG GHYHAHVKTI YKAKKPVQLP GAYNVDIKLD ITSHNEDYTI VEQYERAEAR  240
HSTGG                                                             245

SEQ ID NO: 19            moltype = AA  length = 225
FEATURE                  Location/Qualifiers
source                   1..225
                         mol_type = protein
                         organism = synthetic construct
SEQUENCE: 19
EENNMAIIKE FMRFKVHMEG SVNGYEFEIE GEGERYPYEG TQTARLKVTK GGPLPFAWDI   60
LSPQFMYGSK AYVKHPADIP DYFKLSFPEG FTWERVMNFE DGGVVTVTQD SSLHNGEFIY  120
KVKLLGTNFP SDGPVMQKRT NGWEASTERM YPEDGALKGE INQRLKLKDG GHYHAHVKTI  180
YKAKKPVQLP GAYNVDIKLD ITSHNEDYTI VEQYERAEAR HSTGG               225

SEQ ID NO: 20            moltype = DNA  length = 714
FEATURE                  Location/Qualifiers
source                   1..714
                         mol_type = other DNA
                         organism = synthetic construct
SEQUENCE: 20
gaggaggata acatggcaat tatcaaggaa tttatgcgat ttaaggttca catggagggt   60
tctgttaatg gacacgaatt tgagatcgaa ggagagggtg aaggtcatcc ttacgaggga  120
acacagaccg ctaaattgaa agtcactaaa ggaggacctc ttccattcgc ctgggatata  180
ctttcccctc agtttatgta tggttctaaa gcctatgtca aacatccggc tgacatccca  240
gactatttga agttgtcctt ccccgaaggt tttacatggg aacgcgttat gattttcaag  300
gatcttaagc aacattttg gagtactcct cgaacgacat cgggcggggt cgtcacggtg  360
acacaggact ccagcttgca agatggtgag tttatttata aagtcaagtt attaggtact  420
aatttttccag gggatggacc cattatgcag aaaaagacga tgggctggga ggcatccact  480
gaacgcatgt acccagaaga cggtgcactc aaaggtgaga tcaatcaacg cctcaagctt  540
aaagatggtg gccattacga tgcatgggtt aagacaacat ataaggcaaa aaagcctgtc  600
cagttaccag gcgcctataa cgtggacata aaattgacaa ttacgagcca taacgaggac  660
tacacaatcg tggagcagta tgagcgtgca gagggtcgtc acagtacagg tggc        714
```